United States Patent
Janser et al.

(10) Patent No.: US 7,589,091 B2
(45) Date of Patent: Sep. 15, 2009

(54) HYDROXAMIC ACID DERIVATIVES

(75) Inventors: Philipp Janser, Basel (CH); Wolfgang Miltz, Basel (CH); Ulf Neumann, Rheinfelden (CH)

(73) Assignee: Novartis AG, Basel (CH)

( * ) Notice: Subject to any disclaimer, the term of this patent is extended or adjusted under 35 U.S.C. 154(b) by 382 days.

(21) Appl. No.: 10/511,065

(22) PCT Filed: Apr. 8, 2003

(86) PCT No.: PCT/EP03/03644

§ 371 (c)(1),
(2), (4) Date: Oct. 3, 2005

(87) PCT Pub. No.: WO03/084941

PCT Pub. Date: Oct. 16, 2003

(65) Prior Publication Data

US 2006/0063778 A1 Mar. 23, 2006

(30) Foreign Application Priority Data

Apr. 9, 2002 (GB) .................. 0208176.8

(51) Int. Cl.
*A61K 31/535* (2006.01)
*C07D 295/18* (2006.01)
(52) U.S. Cl. .................. 514/237.5; 544/168
(58) Field of Classification Search ............ 514/237.5; 544/168
See application file for complete search history.

(56) References Cited

U.S. PATENT DOCUMENTS 4,154,937 A  5/1979  Cushman et al.

FOREIGN PATENT DOCUMENTS

| WO | WO 96 33172 | 10/1996 |
| WO | WO 97 22587 | 6/1997 |
| WO | WO 98 27069 | 6/1998 |

OTHER PUBLICATIONS

Devlin et al., J.C.S. Perkin I, (1975), pp. 830-841.*

* cited by examiner

*Primary Examiner*—Rebecca L Anderson
(74) *Attorney, Agent, or Firm*—Hoxie & Associates LLC

(57) ABSTRACT

Novel hydroxamic acid derivatives, e.g., of formula (I), wherein $R_1$, $R_2$, $R_3$ and $R_4$ are as defined, are found to be useful as pharmaceuticals, e.g., for the suppression of TNF release and the treatment of autoimmune and inflammatory diseases, e.g., multiple sclerosis and rheumatoid arthritis. Methods of making the compounds, novel intermediates, and pharmaceutical compositions comprising the compounds are provided.

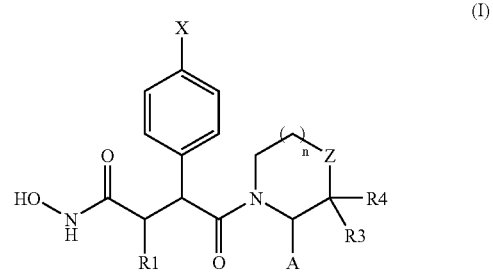

12 Claims, No Drawings

HYDROXAMIC ACID DERIVATIVES

This invention relates to novel hydroxamic acid derivatives and to their use as pharmaceuticals, e.g., in inhibiting matrix metalloproteinases such as collagenase, and in inhibiting TNF production, particularly for treatment of diseases or conditions mediated by over-production of or over-responsiveness to TNFα.

Accordingly the invention provides compounds of Formula I

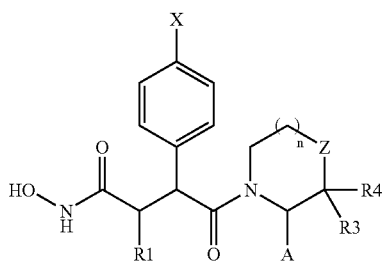

wherein
$R_1$ is lower alkyl, $C_3$-$C_8$cycloalkyl, $C_3$-$C_{18}$heterocycloalkyl or $C_4$-$C_{18}$aryl each of which is independently optionally substituted by hydroxy, halogen, lower alkoxy, $C_3$-$C_8$cycloalkyl-lower alkoxy, or $C_4$-$C_{18}$ aryl-lower alkoxy;

X is halogen, cyano, lower alkyl, halo-substituted lower alkyl, $C_4$-$C_{18}$aryl, $C_4$-$C_{18}$aryl-lower alkyl, hydroxy, —$OR_5$, $SR_5$ or —$NR_6R_7$, each of which is optionally substituted by halogen, hydroxy, lower alkoxy, $C_3$-$C_6$cycloalkyl-lower alkoxy, or $C_4$-$C_{18}$aryl-lower alkoxy
wherein
$R_5$ is hydrogen, lower alkyl, $C_3$-$C_8$cycloalkyl, $C_3$-$C_{18}$heterocycloalkyl or $C_4$-$C_{18}$aryl and
$R_6$ and $R_7$ are independently H, lower alkyl, $C_3$-$C_8$cycloalkyl, $C_3$-$C_{18}$heterocycloalkyl or $C_4$-$C_{18}$aryl;

Z is —$CH_2$—, —$CHR_8$—, —O—, —S—, or —$N(R_8)$—
wherein
$R_8$ is H, lower alkyl, $C_3$-$C_8$cycloalkyl, $C_3$-$C_{18}$heterocycloalkyl, $C_4$-$C_{18}$aryl lower alkoxycarbonyl or $C_4$-$C_{18}$aryloxycarbonyl, each of which is independently optionally substituted by halogen, hydroxy, lower alkoxy, $C_3$-$C_6$cycloalkyl-lower alkoxy, or $C_4$-$C_{18}$aryl-lower alkoxy;

A is hydrogen, —$CR_{10}R_{11}$-Q-$R_{12}$, —C(O)-Q-$R_{12}$ or —C(S)-Q-$R_{12}$
wherein
$R_{10}$ and $R_{11}$ are independently H, lower alky, $C_3$-$C_8$cycloalkyl, $C_3$-$C_{18}$heterocycloalkyl or $C_4$-$C_{18}$aryl each of which is independently optionally substituted by halogen, hydroxy, lower alkoxy, $C_3$-$C_6$cycloalkyl-lower alkoxy, or $C_4$-$C_{18}$ aryl-lower alkoxy, Q is —$NR_8$—, —S— or —O—, where $R_8$ is as defined above, and
$R_{12}$ is lower alkyl $C_3$-$C_8$cycloalkyl, $C_4$-$C_{18}$aryl, $C_4$-$C_{18}$aryl-lower alkyl, each optionally substituted by hydroxy, halogen, lower alkoxy, $C_3$-$C_6$cycloalkyl, $C_3$-$C_6$cycloalkoxy, $C_4$-$C_{18}$aryl or $C_4$-$C_{18}$aryl-lower alkoxy; and $R_3$ and $R_4$ are independently H or lower alkyl
n is 0 or 1, and pharmaceutically-acceptable and -cleavable esters thereof and acid addition salts thereof.

Preferably $R_1$ is H, lower alkyl or $C_3$-$C_8$cycloalkyl, each of which is optionally substituted, preferably by hydroxy, halogen, lower alkoxy or $C_4$-$C_8$aryl-lower alkoxy.

$R_1$ as lower alkyl is preferably $C_1$-$C_4$lower-alkyl e.g. methyl, ethyl or propyl, optionally substituted as defined above, for instance by phenyl-lower alkoxy e.g. as benzyloxymethyl.

$R_1$ as cycloalkyl is preferably $C_3$-$C_6$cycloalkyl, i.e. cyclopropyl, cyclobutyl, cyclopentyl or cyclohexyl, optionally substituted as defined above.

X is preferably halogen, cyano, halo-substituted lower alkyl (e.g. trifluoromethyl), lower alkyl, or lower alkoxy, the latter two of which are independently optionally substituted by halogen, hydroxy or lower alkoxy, X as halogen may be fluorine, chlorine, bromine or iodine, and is preferably fluorine or chlorine.

X as lower alkyl is preferably $C_1$-$C_4$ lower alkyl, e.g. methyl or ethyl, optionally substituted as defined above.

X as lower alkoxy is preferably $C_1$-$C_4$ lower alkoxy e.g. methoxy, or ethoxy, optionally substituted as defined above.

Z is preferably —$CH_2$— or —$N(R'_8)$— wherein $R'_8$ is H, lower alkyl, $C_4$-$C_8$aryl (optionally substituted by halogen), lower alkoxycarbonyl or $C_4$-$C_8$aryloxycarbonyl.

Z as —$N(R'_8)$— is preferably

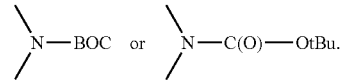

A is preferably H or —C(O)-Q'-$R_{12}'$ wherein
Q' is S or O and $R_{12}'$ is lower alkyl, $C_3$-$C_8$cycloalkyl, $C_4$-$C_8$aryl, each optionally substituted, by hydroxy, halogen, lower alkoxy, $C_3$-$C_6$cycloalkyl, $C_4$-$C_8$aryl,
$R_3$ and $R_4$ are preferably H.
n is preferably 1.

Thus in a preferred embodiment the invention provides a compound of formula II

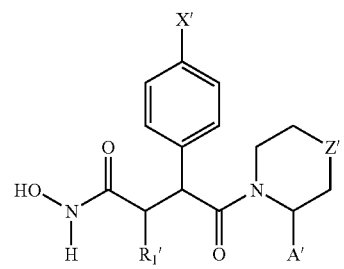

wherein
$R_{1'}$ is H, lower alkyl or $C_3$-$C_8$cycloalkyl, each of which is optionally substituted by hydroxy, halogen, lower alkoxy or $C_4$-$C_8$aryl-lower alkoxy;
X' is halogen, cyano, lower alkyl, halo-substituted lower alkyl or lower alkoxy, each of which is optionally substituted by halogen, hydroxy or lower alkoxy;
Z' is —$CH_2$— or —$N(R'_8)$— wherein $R'_8$ is H, lower alkyl, $C_4$-$C_8$aryl (optionally substituted by halogen), lower alkoxycarbonyl or $C_4$-$C_8$aryloxycarbonyl;

A' is H or —C(O)-Q'-R$_{12}$' wherein Q' is —S— or —O— and R$_{12}$' is lower alkyl, C$_3$-C$_8$ cycloalkyl, C$_4$-C$_8$aryl, each optionally substituted by hydroxy, halogen, lower alkoxy, C$_3$-C$_8$cycloalkyl, or C$_4$-C$_8$aryl, and pharmaceutically acceptable and cleavable esters thereof and acid addition salts thereof.

In particularly preferred compounds of Formula II the substituents R$_1$', X', Z', Q' and R$_{12}$' have the following meanings, independently or in any logical combination thereof:

R$_1$' is ethyl, hydroxymethyl or benzyloxymethyl.

X' is halogen, e.g. chlorine, or lower alkoxy e.g. methoxy.

Z' is —O—,

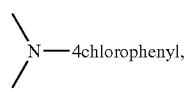

—CH$_2$—, or N-BOC.

A' is H or —C(O)-Q"-R"$_{12}$ wherein

Q" is O, and

R"$_{12}$ is methyl, ethyl, propyl, isopropyl, cyclopropyl, isobutyl, cyclopropylmethyl, sec. butyl, 1,2-dimethylpropyl, 3-methylbutyl, 2-methylbutyl, 2-methoxy-ethyl, 3-methoxy-propyl, 3-isopropoxy-propyl, 2-methoxy-1-methyl-ethyl, 4-hydroxy-cyclohexyl, 2-hydroxy-1-methyl-2-phenyl-ethyl, benzyl, 4-fluorophenyl, 2-hydroxypropyl, 2-methoxy-1-methyl-ethyl, 4-hydroxycyclohexyl, 1-phenylethyl, phenyl, phenylethyl, and 2-hydroxy-propyl.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

Pharmaceutically acceptable esters are, for instance, ester derivatives which are convertible by solvolysis or under physiological conditions to the free carboxylic acids of formula I. Such esters are e.g. lower alkyl esters (such as the methyl or ethyl ester), carboxy-lower all esters such as the carboxymethyl ester, nitrooxy-lower alkyl esters (such as the 4-nitrooxybutyl ester), and the like.

The compounds of formulae I and II, depending on the nature of substituents, may possess one or more asymmetric carbon atoms. The resulting diastereomers and enantiomers are encompassed by the instant invention. Preferably, however, e.g. for pharmaceutical use in accordance with the invention, the compounds of formulae I and II are provided in pure or substantially pure epimeric form, e.g. as compositions in which the compounds are present in a form comprising at least 90%, e.g. preferably at least 95% of a single epimer (i.e. comprising less than 10%, e.g. preferably less than 5% of other epimeric forms).

Preferred are the compounds of formula I' and formula I"

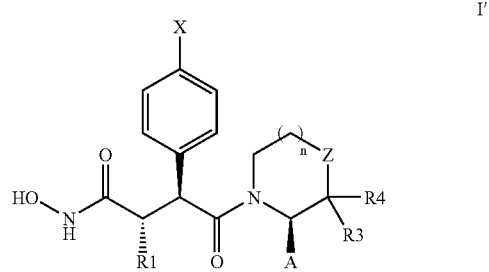

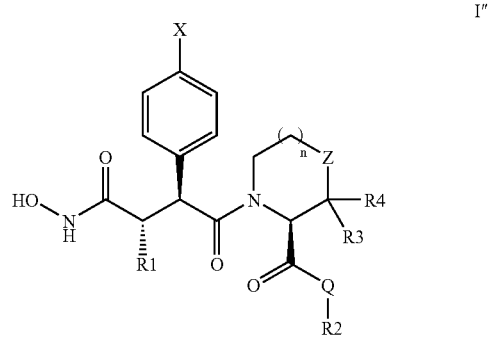

wherein the symbols are as defined above.

Above and elsewhere in the present description the following terms have the meanings given below:

The term "lower" referred to above and hereinafter in connection with organic radicals or compounds respectively defines a compound or radical which may be branched or unbranched with up to and including 7, preferably up to and including 4 and (as unbranched) one or two carbon atoms.

A lower alkyl group is branched or unbranched and contains 1 to 7 carbon atoms, preferably 1-4 carbon atoms. Lower alkyl represents, for example, methyl, ethyl, propyl, butyl, isopropyl or isobutyl.

A lower alkoxy (or alkyloxy) group preferably contains 1-7 carbon atoms, advantageously 1-6 carbon atoms, and represents for example ethoxy, propoxy, isopropoxy, isobutoxy, preferably methoxy. Lower alkoxy includes cycloalkyloxy and cyloalkyl-lower alkyloxy.

Halogen (halo) preferably represents chloro or fluoro but may also be bromo or iodo.

Aryl represents carbocyclic or heterocyclic aryl.

Carbocyclic aryl represents monocyclic, bicyclic or tricyclic aryl, for example phenyl or phenyl mono-, di- or trisubstituted by one, two or three radicals as hereinbefore defined.

Preferred as carbocyclic aryl is naphthyl, phenyl or phenyl mono- or disubstituted as hereinbefore defined.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted, as hereinbefore defined.

Cycloalkyl represents a saturated cyclic hydrocarbon optionally substituted by lower alkyl which contains 3 to 8 ring carbons and is advantageously cyclopropyl, cyclobutyl, cyclopentyl, or cyclohexyl optionally substituted as hereinbefore defined.

Amino may be optionally substituted, e.g. by lower alkyl.

Heterocyclyl represents a saturated cyclic hydrocarbon containing one or more, preferably 1 or 2, hetero atoms selected from O, N or S, and preferably from 3 to 10, more preferably 5 to 8, ring atoms; for example, tetrahydrofuranyl, tetrahydrothienyl, tetrahydropyrrolyl, piperidinyl, piperazinyl or morpholino; all of which may be optionally substituted, for instance as hereinbefore defined.

Aryl-lower alkyl represents preferably (carbocyclic aryl or heterocyclic aryl)-lower alkyl.

Carbocyclic aryl-lower alkyl preferably represents aryl-straight chain or -branched $C_{1-4}$-alkyl in which carbocyclic aryl has meaning as defined above, e.g. benzyl or phenyl-(ethyl, propyl or butyl), each unsubstituted or substituted preferably on the phenyl ring as hereinbefore defined for carbocyclic aryl above, advantageously optionally substituted benzyl.

Heterocyclic aryl-lower alkyl represents preferably straight chain or branched heterocyclic aryl-$C_{1-4}$-alkyl in which heterocyclic aryl has meaning as defined above, e.g. 2-, 3- or 4-pyridylmethyl or (2, 3- or 4-pyridyl)-(ethyl, propyl or butyl); or 2- or 3-thienylmethyl or (2- or 3-thienyl)-(ethyl, propyl or butyl); 2-, 3- or 4-quinolinylmethyl or (2-, 3- or 4-quinolinyl)-(ethyl, propyl or butyl); or 2- or 4-thiazolylmethyl or (2- or 4-thiazolyl)-(ethyl, propyl or butyl).

Cycloalkyl-lower alkyl represents e.g. (cyclopropyl- or cyclobutyl)-(methyl or ethyl).

The invention includes the following compounds:

3(S)-(4-Chloro-phenyl)-2(S)-ethyl-N-hydroxymorpholin-4-yl-4-oxo-butyrmide;

2(R)-Benzyloxymethyl-4-[4-(4chloro-phenyl)-piperazin-1-yl]-N-hydroxy-3(S)-(4-methoxy-phenyl)-4-oxo-butyramide;

2(R)-Benzyloxymethyl-N-hydroxy-3(S)-(4-methoxy-phenyl)-4-oxo-4-piperidin-1-yl-butyramide, N-Hydroxy-2(R)-hydroxymethyl-3(S)-(4-methoxy-phenyl)-4-oxo-piperidin-1-yl-butyramide;

(S)4-[(2S,3S)-2-(4-Chloro-phenyl)-3-hydroxycarbamoyl-pentanoyl]-3-isobutylcarbamoyl-piperazine-1-carboxylic acid .tert.-butyl ester;

(S)-1-[(2S,3S-2-(4-Chloro-phenyl)-3-hydroxycarbamoyl-pentanoyl]-piperazine-2-carboxylic acid isobutyl-amide trifluoro-acetate;

1-[4-Benzyloxy-3(R)-hydroxycarbamoyl-2(S)-(4-methoxy-phenyl)-butyryl]-piperidine-2(S)-carboxylic acid methylamide;

1-[4-Hydroxy-3(R)-hydroxycarbamoyl-2(S)-(4-methoxy-phenyl)-butyryl]-piperidine-2(S)-carboxylic acid methylamide;

1-[3(S)-Hydroxycarbamoyl-2(S)-(4-methoxy-phenyl)-pentanoyl]-piperidine-2(S)-carboxylic acid methylamide;

(S)-1-[(2S,3S)-3-Hydroxycarbamoyl-2-(4-methoxy-phenyl)-pentanoyl]-piperidine-2-carboxylic acid cyclopropylamide;

(S)-1-[(2S,3S)-3-Hydroxycarbamoyl-2-(4-methoxy-phenyl)-pentanoyl]-piperidine-2-carboxylic acid (2-methoxy-ethyl)-amide;

(S)-1-[(2S,3S)-3-Hydroxycarbamoyl-2-(4-methoxy-phenyl)-pentanoyl]-piperidine-2-carboxylic acid (4-hydroxy-cyclohexyl)-amide;

(S)-1-[(2S,3S)-3-Hydroxycarbamoyl-2-(4-methoxy-phenyl)-pentanoyl]-piperidine-2-carboxylic acid benzylamide;

(S)-1-[(2S,3S)-3-Hydroxycarbamoyl-2-(4-methoxy-phenyl)-pentanoyl]-piperidine-2-carboxylic acid (4-fluoro-phenyl)-amide;

(S)-1-[(2S,3S)-2-(4-Chloro-phenyl)-3-hydroxycarbamoyl-pentanoyl]-piperidine-2-carboxylic acid isopropylamide;

(S)-1-[(2S,3S)-2-(4-Chloro-phenyl)-3-hydroxycarbarnoyl-pentanoyl]-piperidine-2-carboxylic acid cyclopropylamide;

(S)-1-[(2S,3S)-2-(4-Chloro-phenyl)-3-hydroxycarbamoyl-pentanoyl]-piperidine-2-carboxylic acid (3-isopropoxy-propyl)-amide;

(S)-1-[(2S,3S)-2-(4-Chloro-phenyl)-3-hydroxycarbamoyl-pentanoyl]-piperidine-2-carboxylic acid (4-hydroxy-cyclohexyl)-amide;

(S)-1-[(2S,3S)-2-(4-Chloro-phenyl)-3-hydroxycarbamoyl-pentanoyl]-piperidine-2-carboxylc acid benzylamide;

(S)-1-[(2S,3S)-2-(4-Chloro-phenyl)-3-hydroxycarbamoyl-pentanoyl]-piperidine-2-carboxylic acid phenylamide;

1-[3(S)-Hydroxycarbamoyl-2(S)-(4-methoxy-phenyl)-pentanoyl]-pyrrolidine-2(S)-carboxylic acid phenylamide;

(S)-1-[(2S,3S)-2-(4-Chloro-phenyl)-3-hydroxycarbamoyl-pentanoyl]-pyrroldine-2-carboxylic acid ((S)-2-hydroxypropyl)-amide.

The compounds of formula I, II, I' and I" and the specific compounds listed above are hereinafter referred to as Compounds of the Invention.

Compounds of the Invention of Formula I are obtained by conversion of a corresponding free carboxylic acid derivative of formula V

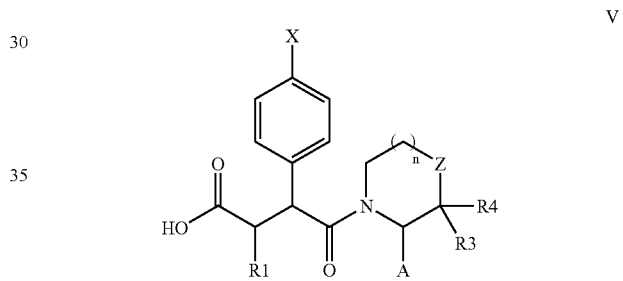

wherein the symbols are as defined above, to the corresponding hydroxamic acid derivative of formula I.

An acid of formula V is converted to an activated acid. For example an acid of formula V is dissolved in an inert solvent, such as dichloromethane, HOPO and 4-(2-isocyano-ethyl)-morpholine are added successively. The activated acid is then treated with a protected amino alcohol; for example, a silyl protected amino alcohol e.g. TMSONH$_2$, to yield a compound of formula I The free carboxylic acid derivatives of formula V are prepared by oxidation of a corresponding olefin derivative of formula VI

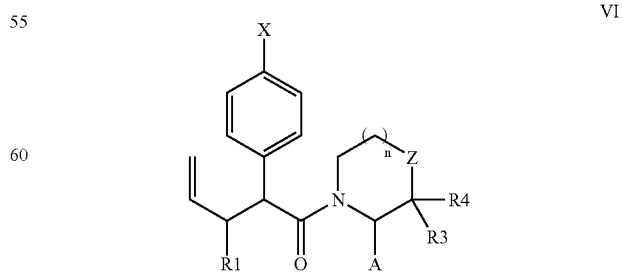

wherein the symbols are as defined above.

For example the crude olefin of formula VI is dissolved in a polar inert non-aqueous solvent such as lower aliphatic alcohol, advantageously methanol and preferably cooled e.g. −85° C.−−65° C. Ozone is introduced preferably at a reduced temperature e.g. −80° C.−−60° C. The solution is then purged with an inert gas such as nitrogen and treated with dimethylsulfide. The solvent is removed and the crude oil redissolved in a polar inert solvent such as lower aliphatic alcohol, advantageously t-butanol. A solution of sodium dihydrogenphosphate monohydrate in a polar solvent such as water is added, followed by 2-methyl-2-butene and sodium chlorite in a polar solvent such as water. When the reaction has ceased the reaction mixture is treated with sodium sulfite in a polar solvent such as water to yield a compound of the formula V The olefin derivatives of formula VI are advantageously prepared by coupling of olefin derivatives of formula VII

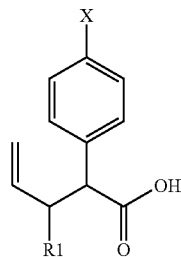

VII with a N-heterocycle derivative of formula VIII

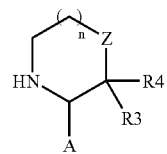

VIII wherein the symbols are as defined above.

For example a N-heterocycle derivative of formula VIII and an olefin derivative of formula VII are dissolved in a polar solvent such as DMP and preferably cooled e.g. −10° C.-10° C. HOBT, lower alkylamine such as triethylamine and a coupling reagent such as EDC are added successively. The reaction mixture is allowed to warm to room temperature. To yield a compound of formula VI The olefin precursors of formula VII are prepared by rearrangement of a precursor compound of formula IX

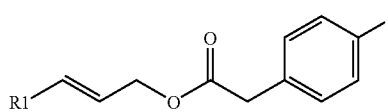

IX wherein the symbols are as defined above

For example hexamethyl disilazan is dissolved under an inert atmosphere such as argon in a polar inert non-aqueous solvent such as THF and preferably cooled e.g. −10° C.-10° C. A lower alkyllithium such as n-Butyl lithium in an inert solvent such as hexane is added. The reaction mixture is preferably cooled further e.g. −68° C.−−88° C. and a lower alkylchlorosilane such as trimethyl chlorosilane is added, followed by addition of a solution of a compound of formula IX in a polar inert non-aqueous solvent such as THF. Titanium tetrachloride in and inert solvent such as dichloromethane is added and the reaction mixture preferably allowed to warm up e.g. to room temperature to yield a compound of formula VII The derivatives of formula VIII are prepared by a deprotection of a protected carboxylic acid of formula XII

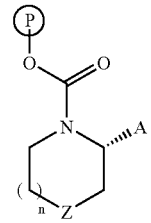

XII wherein the symbols are as defined above or in the case of (P) as defined below. (P) is a carboxylic acid protecting group which may be a silyl protecting group (e.g. tertiarybutyldimethylsilyl or trimethylsilyl), or any other carboxylic acid protecting group commonly known in the art.

For example the amide of formula XII is treated with a lower alkanoic acid such as trihalo acetic acid for example trifluroacetic acid TFA at a reduced temperature preferably −10° C.-10° C. The mixture is evaporated and HCl is added to yield a compound of formula XII Compounds of the Invention, as defined above, e.g., of formula I, II, I' and I" and particularly as exemplified, in free or pharmaceutically acceptable ester and salt form, exhibit pharmacological activity and are useful as pharmaceuticals, e.g. for therapy, in the treatment of diseases and conditions as hereinafter set forth.

As discussed in the test procedures described below, the Compounds of the Invention are potent inhibitors of TNFα release, are orally active, and are not cytotoxic at their effective doses. The Compounds of the Invention also inhibit collagenase and stromelysin at concentrations of from 0.3 to 10 nM and are shown to be good inhibitors of mechanical hyperalgesia. The Compounds of the Invention tested further show oral activity in vivo at dosages of less than 10 mg/kg in LPS induced TNFα release in the rat, and appear to be well tolerated at such dosages.

Test Procedure 1: Inhibition of TNF release

Mononuclear cells are prepared from the peripheral blood of healthy volunteers using ficoll-hypaque density separation according to the method of Hansell et al., J. Imm. Methods (1991) 145: 105, and used at a concentration of $10^5$ cells/well in RPMI 1640 plus 10% FCS. Cells are incubated with serial dilutions of the test compounds for 30 minutes at 37° C. prior to the addition of IFNγ (100 U/ml) and LPS (5 μg/ml) and subsequently further incubated for three hours. Incubation is terminated by centrifugation at 1400 RPM for 10 min. TNFα in the supernatant is measured using a commercial ELISA (Innotest hTNFα, available from Innogenetics N.V., Zwijnaarde, Belgium). Compounds of the Invention are tested at concentrations of from 0 to 10 μM. Exemplified compounds of formula I, especially of formula Ia, suppress TNF release in this assay with an $IC_{50}$ of from about 50 nM to about 5 μM.

Test Procedure 2: Cytotoxicity

Cytotoxicity is determined on THP1 cells ($5\times10^4$/well) which are incubated in the presence of IFNγ (100 U/ml) and LPS (5 μg/ml) and presence and absence of test compound for 24 hours at 37° C. Percentages of living and dead cells are assessed by a colorimetric readout (MTT), which measures mitochondrial dehydrogenase enzymes in living cells, as described in Mosman, J. Imm. Methods (1983) 65: 55. Compounds of the Invention tested show less than 50% cytotoxicity at a concentration of 10 μM, showing that the Compounds of the Invention are not cytotoxic at concentrations sufficient to suppress TNF.

Test Procedure 3: Collagenase Inhibition

Collagenase inhibition is determined using active collagenase with the thiopeptide MMP-substrate described in Stein and Izquierdo-Martin, Arch. Biochem. Biophys. 308 (1994) pp. 274-277. Test compound is incubated with the collagenase prior to the addition of the substrate at pH 6.5, 25° C. in 2-morpholinoethanesulphonic acid (50 mM) buffer with 10 mM $CaCl_2$. The absorbance is recorded at 405nm at regular intervals for a period of 40 minutes. The inhibitory activity of the test compound is determined as a function of the collagenase activity in the control in the presence and absence of the test compound. Compounds of the Invention show significant dose dependent inhibition of collagenase at low nM concentrations, e.g., below 10 nM.

Test Procedure 4: Oral Bioavailability

The assay of the preceding example is standardized by measuring activity of varying known concentrations of a particular test compound and used to measure the concentration of test compound in plasma following oral administration. Test compounds are administered orally to conscious rats at a dosage of 10 mg/kg. Blood samples are taken from the cut tip of the tail at 30, 60, 120, and 240 minutes from oral administration. The plasma is subjected to trichloroacetic acid extraction. The extract is tested in the above collagenase inhibition assay to obtain an estimate of the concentration of drug present in the plasma Compounds of the Invention show good oral bioavailability, with plasma concentrations of 300-5000 nM after 30 minutes and 50-500 nM after 240 minutes. Thus, pharmaceutically effective plasma levels (as shown in Test Example 1 and 3) are readily achievable with oral administration at manageable dosages, e.g., 10 mg/kg. Moreover, the plasma levels obtained are well below the cytotoxic level, and the rats were not observed to show any adverse effects at this dosage.

Test Procedure 5: Effect on Mechanical Hyperalgesia and Allodynia

The effect on mechanical hyperalgesia and allodynia is determined using a model of neuropathic pain in rat (Seltzer et al, 1990). A 7-0 silk suture is inserted into the sciatic nerve of one of the hind-paws, usually the left, causing mechanical hyperalgesia and allodynia to be induced. Mechanical hyperalgesia is measured by the paw withdrawal thresholds of the hind-paws to increasing pressure stimulus using an Analgesymeter. Mechanical allodynia is measured by the withdrawal thresholds of the hind-paws to non-noxious mechanical stimuli applied using von Frey hairs. Test compound or vehicle (20% cremaphor/water) was administered orally twice daily for 7 days commencing from the day of surgery. Paw withdrawal thresholds of vehicle treated animals was approximately 60 g and paw withdrawal thresholds of test compound treated animals increased, with repeated dosing, to 80-90 g. Three days after the end of test compound administration the paw withdrawal threshold of the test compound treated animals remained elevated above that of the vehicle treated animals. Treatment with test compound prior to surgery and a further single treatment with the test compound after surgery had a significant degree of inhibition of hyperalgesia lasting several days. Compounds of the invention tested were also effective in the inhibition of established mechanical hyperalgesia. After just four days of administration of test compound, to animals with established mechanical hyperalgesia, there was a significant increase in the paw withdrawal threshold compared to the vehicle treated animals.

Accordingly, Compounds of the Invention have pharmaceutical utility as follows:

Compounds of the Invention are useful for the prophylaxis and treatment of diseases or pathological conditions mediated by TNF, especially TNFα, e.g., inflammatory conditions, autoimmune diseases, severe infections, and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants.

Compounds of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which Compounds of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Compounds of the Invention are also useful for the treatment, prevention, or amelioration of asthma, bronchitis, pneumoconiosis, pulmonary emphysema, and other obstructive or inflammatory diseases of the airways.

Compounds of the Invention are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

In addition to inhibiting the release of TNF, especially TNFα through the suppression of TNF convertase, Compounds of the Invention are also inhibitors of matrix metalloproteinases, e.g., collagenase, stromelysin and gelatinases, and hence useful for the indications known for collagenase inhibitors or other matrix metalloproteinase inhibitors, e.g., treatment of various pathological conditions of the skin, bones, and connective tissues, e.g., rheumatoid arthritis, psoriasis, psoriatic arthritis, osteoporosis, osteoarthritis, periodontitis, gingivitis, and corneal ulceration; for the treatment of cardiovascular disease, e.g., atherosclerosis, and coronary angioplasty; for the prevention of tumor cell metastasis and invasion and in inducing fibrosis of tumors, e.g., in the treatment of cancer; and for the prevention of neurodegenerative disorders, e.g., Alzheimer's disease.

Compounds of the Invention in addition to inhibiting the release of TNF, especially TNFα through the suppression of TNF convertase, and the inhibition of matrix metalloprotinases, are also inhibitors of neuropathic pain and associated hyperalgesia and are hence useful for the indications known for neuropathic pain inhibitors, e.g., treatment of neuropathic pain and associated hyperalgesia, including trigeminal and herpetic neuralgia, diabetic neuropathic pain, migraine, causalgia and defferentation syndromes such as brachial plexus avulsion.

For the indications described above the appropriate dosage will, of course, vary depending, for example, on the particular Compound of the Invention employed, the subject to be treated, the mode of administration and the nature and severity of the condition being treated. However, in general, satisfactory results in animals are obtained at daily dosages of from about 0.1 to about 100 mg/kg/day p.o. In larger mammals, for example humans, an indicated daily dosage is in the range of from about 5 to about 1000 mg of Compound of the Invention administered orally once or, more suitably, in divided dosages two to four times/day.

Compounds of the Invention may be administered by any conventional route, e.g. orally, for example in the form of solutions for drinking, tablets or capsules or parenterally, for example in the form of injectable solutions or suspensions. Normally for systemic administration oral dosage forms are preferred, although for some indications Compounds of the Invention may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg Compound of the Invention per unit dosage.

In accordance with the foregoing the present invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of a Compound of the Invention, or a method of treating any of the above mentioned conditions, particularly a method of treating an inflammatory or autoimmune disease or condition, e.g., multiple sclerosis or rheumatoid arthritis, or alleviating one or more symptoms of any of the above mentioned conditions.

B. A method of inhibiting neuropathic pain and associated hyperalgesia in a subject (i.e. a mammal, especially a human) in need of such treatment which method comprises administering to said subject an effective amount of a compound of the invention, or a method of treating any of the above mentioned disease or conditions, e.g., neuropathic pain and associated hyperalgesia, diabetic neuropathic pain or migraine, or alleviating one or more symptoms of any of the above mentioned conditions.

C. B. A Compound of the Invention for use as a pharmaceutical, e.g. for use as an immunosuppressant, antiinflammatory or neuropathic pain relief agent or for use in the prevention, amelioration or treatment of any disease or condition as described above, e.g., an autoimmune, inflammatory or neuropathic pain disease or condition.

D. C. A pharmaceutical composition comprising a Compound of the Invention in association with a pharmaceutically acceptable diluent or carrier, e.g., for use as an immunosuppressant, anti-inflammatory or neuropathic pain relief agent or for use in the prevention, amelioration or treatment of any disease or condition as described above, e.g., an autoimmune, inflammatory or neuropathic pain disease or condition.

E. D. Use of a Compound of the Invention in the manufacture of a medicament for use as an immunosuppressant, anti-inflammatory or neuropathic pain relief agent or for use in the prevention, amelioration or treatment of any disease or condition as described above, e.g., an autoimmune, inflammatory or neuropathic pain disease or condition.

Abbreviations used herein in relation to the invention:
BOC: Benzyloxycarbonyl
DCC: Dicyclohexyl-carbodiimide
DMAP: Dimethyl-pyridin-4-yl-amine
DMF: N,N-Dimethyl formamide
EDC: (3-Dimethylamino-propyl)-ethyl-carbodiimide hydrochloride
HCl: Hydrochloric acid
HOBT: Benzotriazol-1-ol
HOPO: 1-Oxy-pyridin-2-ol
MEI: 4-(2-Isocyano-ethyl)-morpholine
NaOH: Sodium hydroxide
TBME: t-Butyl methyl ether
TFA: Trifluoro-acetic acid
THF: Tetrahydrofuran
TMSONH2: O-(Trimethylsilyl)-hydroxylamine

REACTION SCHEME

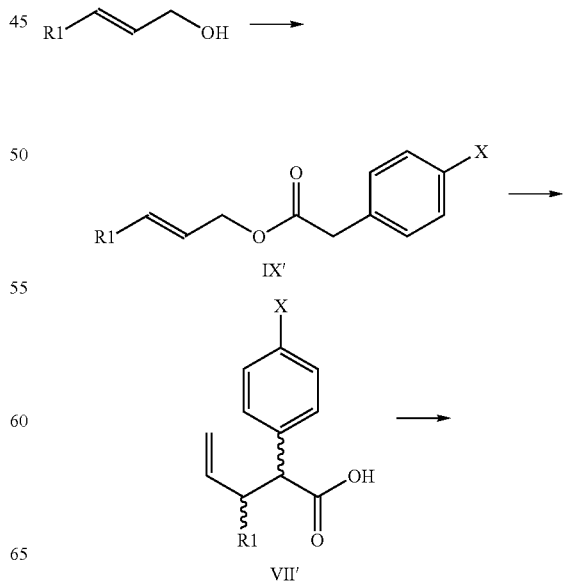

13

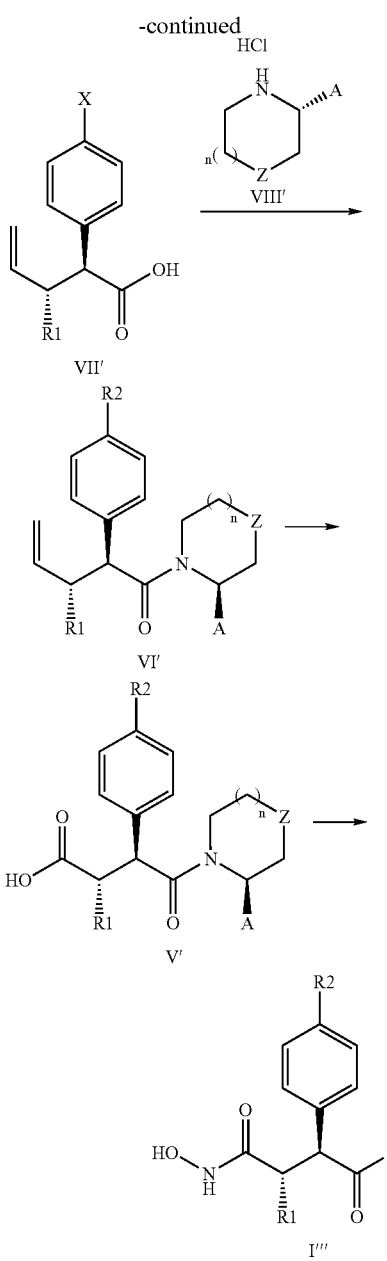

Synthesis of the Intermediates VII'

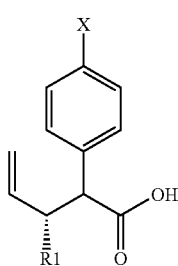

14

The intermediates of formula VII' were prepared by the general Method IA which comprises the coupling of a suitable allylic alcohol with the corresponding phenyl-acetic acid, followed by an adapted Ireland-Claisen rearrangement and optical resolution of the enantiomers using (S)-(−)-1-phenyl-ethylamine.

Method IA is illustrated by the following representative examples.

EXAMPLE I1

3(R)-Benzyloxymethyl-2(S)-(4-methoxy-phenyl)-pent-4-enoic acid (I1)

Step A: Prop-2-ynyloxymethyl-benzene (I1a)

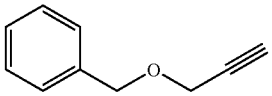

Tetrabutylammonium bromide (19.34 g, 600 mmol) was added to a solution of benzylbromide (71.3 ml, 600 mmol) and propargyl alcohol (35.5 ml, 600 mmol) in 270 ml of toluene and the mixture was heated to 50° C. A solution of sodium hydroxide (24 g, 600 mmol) in 55 ml of water was then added dropwise over a period of 1 hour and stirring was continued for another 3 hours. The reaction mixture was then cooled to 25° C. and transferred into a separatory funnel. The aqueous layer was removed and the organic layer was washed three times with 150 ml of brine. Residual water was removed by repeated azeotropic distillation using toluene. A pale yellow liquid was obtained. Yield: 81.9 g (93.4 %).

MS (EI): 145 [M−H]− $^1$H NMR (CDCl$_3$), δ (ppm): 7.29-7.40 (m, 5H), 4.64 (s, 2H), 4.20 (d, 2H), 2.49 (t, 1H).

Step B: 4-Benzyloxy-but-2-yn-1-ol (I1b)

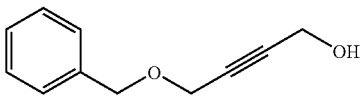

The crude alkyne I1 (81.9 g, 560 mmol) was dissolved in 500 ml of THF and cooled to −78° C. A 2.5M solution of n-hexyl lithium (250 ml, 625 mmol) was added dropwise over a period of 2 hours, so that the temperature did not exceed −70° C. Stirring was continued for 3 hours at −78° C. and then solid paraformaldehyde (20.18 g, 672 mmol) was added. The dry ice-bath was removed and the reaction allowed to warm up to room temperature over night (approx. 20 hours). The mixture was diluted with 600 ml of TBME and extracted with 400 ml of an ammonium chloride solution (20%). The aqueous layer was extracted once more with 200 ml of TBME and the combined organic fractions were washed three times with 400 ml of a brine, dried over anhydrous sodium sulfate and evaporated to give an orange liquid. Yield: 87.9 g (89%).

$^1$H NMR (CDCl$_3$), δ (ppm): 7.25-7.40 (m, 5H), 4.62 (s, 2H), 4.35 (t, 2H), 4.24 (t, 2H).

Step C: trans-4-Benzyloxy-but-2-en-1-ol (I1c)

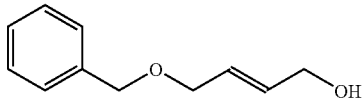

Commercial Red-Al (70% in toluene) (85.2 g, 295 mmol) was added dropwise to a cooled (−2° C.) solution of crude alcohol I1b (40 g, 227 mmol) dissolved in 200 ml of THF. The temperature was kept below 5° C. during the addition. After 1 hour the reaction had ceased and a fine suspension formed which was added dropwise to 300 ml of ice cold 20% sulfuric acid. The resulting suspension was diluted with 250 ml of toluene and stirred vigorously for 30 minutes. The two layers were then separated and the aqueous phase extracted again with of toluene. The combined organic layers were washed with saturated sodium bicarbonate solution and brine, evaporated and dried by repeated azeotropic distillation using toluene. An orange brown liquid was obtained which was distilled under reduced pressure (110° C., 0.05 mbar). Yield: 32.65 g (80.7%).

$^1$H NMR (CDCl$_3$), δ (ppm): 7.15-7.35 (m, 5H), 5.65-5.90 (m, 2H), 4.46 (s, 2H), 4.09 (br. d, 2H), 3.97 (d, 2H).

Step D: trans-(4-Methoxy-phenyl)-acetic acid 4-benzyloxy-but-2-enyl ester (I1d)

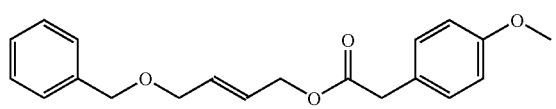

DMAP (3.425 g, 28 mmol) was added to a suspension of the alcohol I1c (100 g, 560 mmol) and (4-methoxy-phenyl)-acetic acid (93.05 g, 560 mmol) in 425 ml of toluene. After 15 minutes of stirring a yellow solution was formed. A solution of DCC (115.55 g, 560 mmol) in 225 ml of DMP was added dropwise during 25 minutes. Eventual cooling was required to keep the temperature between 23 and 27° C. Stirring was continued for 1 hour. Then, heptane (225 ml) was added, the suspension was cooled to −5° C., filtered and washed with 300 ml of cold heptane. The filtrate was washed twice with 1000 ml of water, filtered through basic aluminium oxide (ALOX, 500 g) and evaporated to give a yellow oil. Yield: 161.4 g (88%).

MS (EI): 349 [M+Na]$^+$ $^1$H NMR (CDCl$_3$), δ (ppm): 6.60-7.20 (m, 9H, 5.65 (m, 2H), 4.40 (t, 2H), 4.31 (s, 2H), 3.82 (d, 2H), 3.58 (s, 3H), 3.38 (s, 2H).

Step E: 3-Benzyloxymethyl-2-(4-methoxy-phenyl)-pent-4-enoic acid (I1e)

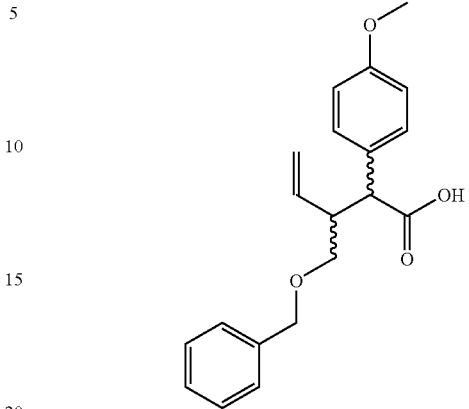

A solution of hexamethyl disilazane (38.4 ml, 184.3 mmol) in 100 ml of THF is cooled to 0° C. under nitrogen. Hexamethyl lithium (26.6% in hexane, 63.65 g, 184 mmol) was added over 15 minutes at a temperature below 4° C. The mixture was cooled to −78° C. and trimethyl chlorosilane (22.65 ml, 184 mmol) was added dropwise over 15 minutes followed by a solution of the ester I1d (50 g, 153.2 mmol) in 50 ml of THF (over 45 minutes). Finally, titanium tetrachloride (1M in toluene, 310 μl, 0.31 mmol) was injected and the brown mixture was allowed to warm to 20° C. over a period of 90 minutes. Stirring was continued for another hour and the resulting mixture was poured into 400 ml of 1N-NaOH. The aqueous layer was separated and the organic layer was extracted with another 70 ml portion of 1N-NaOH. The combined aqueous layers were acidified with 390 ml of 5%-HCl and extracted with toluene (300 ml) which was then evaporated to give the title compound as a racemic mixture of diastereomers (syn/anti ratio of 13/1). Yield: 38.35 g (76.7%)

Step F: 3(R)-Benzyloxymethyl-2(S)-(4-methoxy-phenyl)-pent-4-enoic acid (I1)

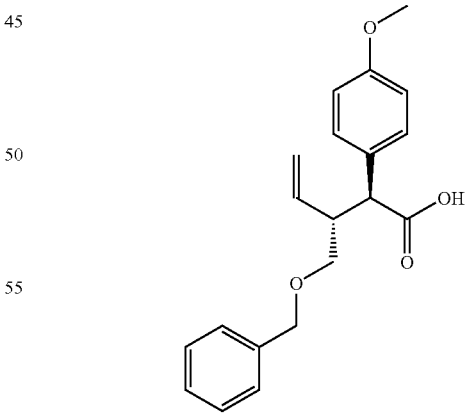

A solution of crude acid I1e (45.17 g, 138.3 mmol) in 1850 ml of ethyl acetate was treated with of (S)-(−)-1-phenyl-ethylamine (18.4 g, 152.2 mmol). A white precipitate was formed immediately, which dissolved upon heating to reflux. The solution was allowed to cool down to 20° C. over a period of 4 hours. The formed crystals (25.35 g, 41%) were filtered off, dried under vacuum and recrystallized from 1125 ml of ethyl acetate to give 15.7 g (25%) of enantiomerically pure salt. This material was suspended in 350 ml of toluene and extracted with 100 ml of 1N-HCl. The organic layer was washed twice with water and evaporated to give a viscous oil which solidified upon standing. Yield: 11.3 g (99%).

MS (EI): 325 [M–H]⁻ ¹H NMR (CDCl₃), δ (ppm): 6.70-7.40 (m, 9H), 5.40 (m, 1H), 4.87 (m, 2H), 4.43 (s, 2H), 3.71 (s, 3H, overlapping with d, 1H), 3.50 (d×d, 1H), 3.37 (d×d, 1H), 3.09 (m, 1H).

EXAMPLE I2

2(S)-(4-Chloro-phenyl)-3(R)-ethyl-pent-4-enoic acid (I2)

Step A: (4-Chloro-phenyl)-acetic acid pent-2-enyl ester (I2a)

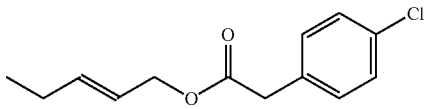

Trans-2-penten-1-ol (49.6 ml; 487.6 mmol) and (4-chloro-phenyl)-acetic acid (83.2 g; 487.6 mmol) were dissolved in 1200 ml of dichloromethane. After addition of EDC (140.2 g, 731 mmol) and DMAP (11.9 g, 97.5 mmol), the reaction mixture was stirred for 18 hours at room temperature. After evaporation under reduced pressure, the residue was dissolved with diethyl ether, washed with water, brine and dried over anhydrous sodium sulfate. Evaporation gave 136 g of an yellow oil, which was further purified by flash-chromatography (silica gel; hexane/ethyl acetate 9:1). Yield: 68 g (59%).

¹H-NMR (CDCl₃): δ (ppm) 7.25 (d, 2H), 7.15 (d, 2H), 5.68-5.78 (m, 1H), 5.42-5.52 (m, 1H), 4.47 (d, 2H), 3.52 (s, 2H), 2.0 (q, 2H), 0.92 (t, 3H).

Step B: 2-(4-Chloro-phenyl)-3-ethyl-pent-4-enoic acid (I2b)

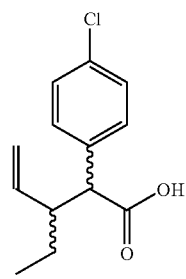

Hexamethyl disilazan (20.3 g, 126 mmol) was dissolved under argon in 200 ml of dry THF and cooled to 0° C. n-Butyl lithium (1.6M in hexane, 79 ml, 126 mmol) was added dropwise and stirred for 10 minutes at 0° C. The reaction mixture was cooled to −78° C. and trimethyl chlorosilane (16 ml, 126 mmol) was added via syringe, followed by addition of a solution of I2a (20 g, 83.8 mmol) in 50 ml of THF. After stirring for 1 hour at −78° C., titanium tetrachloride (1M in dichloromethane, 1.7 ml, 1.7 mmol) was added via syringe and the reaction mixture was allowed to warm up to room temperature, and was stirred for 1 hour. The mixture was evaporated and the residue was dissolved in diethyl ether and extracted twice with 1N-NaOH. The aqueous layer was acidified with 1N-HCl and extracted with diethyl ether. The organic layers were dried over anhydrous sodium sulfate and evaporated under reduced pressure. Yield: 17.3 g of white crystals (87%) as a racemic mixture of diastereomers (syn/anti ratio of 9/1).

Step C: 2(S)-(4-Chloro-phenyl)-3(R)-ethyl-pent-4-enoic acid (I2)

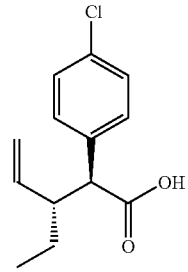

A hot solution of the racemate I2b (17.3 g, 72.5 mmol) in ethanol (250 ml) was treated with (S)-(–)-1-phenyl-ethylamine (10.1 ml, 72.5 mmol). After slowly cooling down, the precipitate was filtered off and recrystallized from ethanol. Yield: 5.7 g of white crystals. The salt was treated with 2N HCl and the free acid was extracted with ethyl acetate. Yield: 3.8 g (17%).

¹H-NMR (CDCl₃): δ (ppm) 7.03-7.17 (4H, m), 5.08 (m, 1H), 4.75 (d×d, 1M), 4.65 (d×d, 1H), 3.3 (d, 1H), 2.48 (d×q, 1H), 1.4-1.5 (m, 1H), 1.1-1.2 (m, 1H), 0.75 (t, 3H).

EXAMPLE I3

2(S)-(4-Methoxy-phenyl)-3(R)-ethyl-pent-4-enoic acid (I3)

Step A: (4-Methoxy-phenyl)-acetic acid pent-2-enyl ester (I3a)

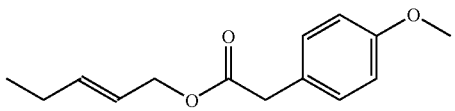

The ester I3a was prepared as described in Step A of example I2, using trans-2-penten-1-ol (49.6 ml; 487.6 mmol) and (4methoxy-phenyl)-acetic acid (81 g; 487.6 mmol) Yield: 57.7 g (52%) of a yellow oil.

¹H-NMR (CDCl₃): δ (ppm) 7.13 (d, 2H), 6.78 (d, 2H), 5.68-5.78 (m, 1H), 5.42-5.52 (m, 1H), 4.45 (d, 2H), 3.72 (s, 3H), 3.5 (s, 2), 2.0 (q, 2H), 0.92 (t, 3H).

Step B: 2-(4-Methoxy-phenyl)-3-ethyl-pent-4-enoic acid (I3b)

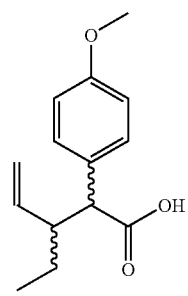

Acid I3b was prepared as described in Step B of example I2, using hexamethyl disilazan (20.7 g, 128 mmol), n-butyl lithium (1.6M in hexane, 80 ml, 128 mmol), trimethyl chlorosilane (16.2 ml, 128 mmol), I3a (20 g, 85.4 mmol) and titanium tetrachloride (1M in dichloromethane, 1.7 ml, 1.7 mmol). Yield: 15.9 g of white crystals (80%) as a racemic mixture of diastereomers (syn/anti ratio of 9/1).

Step C: 2(S)-(4-Methoxy-phenyl)-3(R)-ethyl-pent-4-enoic acid (I3)

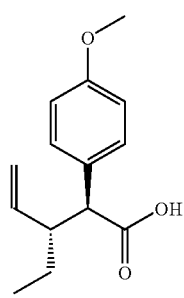

A hot solution of the racemate I3b (15.9 g, 67.4 mmol) in ethanol (300 ml) was treated with (S)-(−)-1-phenyl-ethylamine (9.4 ml, 67.4 mmol). After slowly cooling down, the precipitate was filtered off and recrystallized from ethanol. Yield: 6.2 g of white crystals. The salt was treated with 2N-HCl and the free acid was extracted with ethyl acetate. Yield: 4.1 g (26%).

$^1$H-NMR (CDCl$_3$): δ (ppm) 7.05 (d, 2H), 6.67 (d, 2H), 5.18-5.08 (m, 1H), 4.73 (d×d, 1H), 4.68 (d×d, 1H), 3.62 (s, 3H), 3.27 (d, 1H), 2.5 (m, 1H), 1.4-1.5 (m, 1H), 1.1-1.2 (m, 1H), 0.75 (t, 3H).

Synthesis of the Secondary Amines VIII'

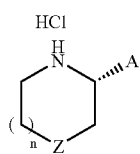

VIII'

The secondary amines of the formula VIII' were prepared by the general Method IB which comprises a standard coupling of an appropriate amine with the corresponding protected carboxylic acid, followed by cleavage of the protecting group.

Method IB is illustrated by the following representative examples.

EXAMPLE I4

(S)-Pyrrolidine-2-carboxylic acid phenylamide (I4)

Step A: 2(S)-Phenylcarbamoyl-pyrrolidine-1-carboxylic acid t-butyl ester (I4a)

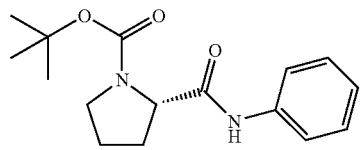

A solution of pyrrolidine-1,2(S)-dicarboxylic acid 1-t-butyl ester (50 g, 233 mmol), EDC (45 g, 233 mmol) and HOBT (12 g, 77.5 mmol) in 1500 ml of dichloromethane was cooled to 0° C. and aniline (21 ml, 233 mmol) was added dropwise over a period of 15 minutes. The mixture was stirred over night, evaporated and partitioned between ethyl acetate and 1N-HCl. The organic layer was washed with saturated sodium bicarbonate solution and brine, dried over anhydrous sodium sulfate and evaporated. The crude solid was crystallized from diethyl ether. Yield: 104 g (quantitative).

Step B: (S)-Pyrrolidine-2-carboxylic acid phenylamide (I4)

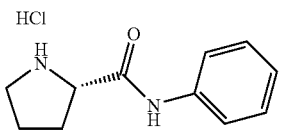

The amide I4a (64 g, 220 mmol) was treated with 150 ml of TFA (95%) at 0° C. for 1 hour. The mixture was evaporated and 600 ml of 1N-HCl was added. After stirring for 30 minutes, the solvent was again evaporated. The crude was dried by repeated azeotropic distillation with toluene. Crystallization from diethyl ether afforded white crystals. Yield: 47 g (94%).

EXAMPLE I5

Piperidine-2(S)-carboxylic acid methylamide hydrochloride (I5)

Step A: 2(S)-Methylcarbamoyl-piperidine-1-carboxylic acid t-butyl ester (I5a)

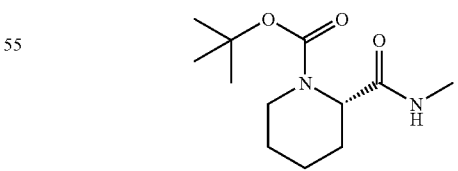

BOC-protected L-pipecolinic acid (5 g, 21.81 mmol), which was prepared according to the procedure described by Ponnusamy et al. (Synthesis (1986), 48-49), was dissolved in 50 ml of THF and cooled to −75° C. Then, 1-Hydroxy-pyrrolidine-2,5-dione (2.51 g, 21.81 mmol) was added, followed by a solution of DCC (4.5 g, 21.81 mmol) in 20 ml of THF (which was added during a period of 45 minutes). The mixture was stirred for 3 hours, then methyl amine (40% in water, 1.9 ml, 21.81 mmol) was added and stirring continued over the weekend. The suspension was filtered, washed with ethyl acetate and evaporated. The crude residue was redissolved in ethyl acetate and extracted with 0.1N-HCl, 5% sodium bicarbonate and brine. After drying over anhydrous sodium sulfate and evaporation a sticky oil was obtained. Yield: 4.71 g (89%).

Step B: Piperidine-2(S)-carboxylic acid methylamide hydrochloride (I5)

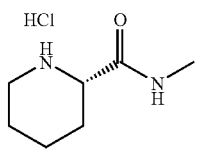

Crude amide I5a (4.7 g, 19.4 mmol) was dissolved in 20 ml of dioxane and cooled in an ice-bath. Then, a 4M-solution of HCl in dioxane (9.7 ml, 38.8 mmol) was added and the mixture was stirred over night. The solvent was then evaporated under reduced pressure to give a white solid. Yield: 3.3 g (97%).

MS (EI): 142 [M]$^+$ $^1$H-NMR (DMSO-d$_6$): δ (ppm) 9.3 (broad s, 1H), 8.65 (broad s, 1H), 8.55 (broad s, 1H), 3.7 (broad s, 1H), 3.2 (m, 1H), 2.85 (m, 1H), 2.64 (d, 3H), 2.05 (m, 1H), 1.35-1.8 (m, 5H).

EXAMPLE I6

(S)-Pyrrolidine-2-carboxylic acid ((S)-2-hydroxy-propyl)-amide hydrochloride (I6)

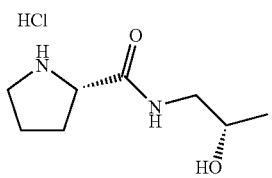

Compound I6 was prepared by EDC/HOBT-coupling of (S)-2-hydroxy-propylamine with pyrrolidine-1,2(S)-dicarboxylic acid 1-t-butyl ester (analogous to Step A of Example 14), followed by HCl-cleavage in dioxane (Step B of Example I5). The crude salt was used as such.

MS (neg. ESI): 207 [M+Cl]−, (ESI): 173 [M+H]+

EXAMPLE I7

(S)-Piperidine-2-carboxylic acid (2-methoxy-ethyl)-amide hydrochloride (I7)

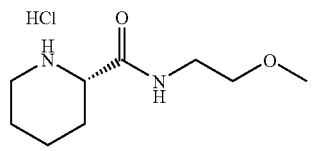

Compound I7 was prepared analogous to Example I6, starting from 2-methoxy-ethylamine and BOC-protected L-pipecolinic acid. The crude salt was used as such.

MS (ESI): 187 [M+H]+

EXAMPLE I8

(S)-Piperidine-2-carboxylic acid (3-isopropoxy-propyl)-amide hydrochloride (I8)

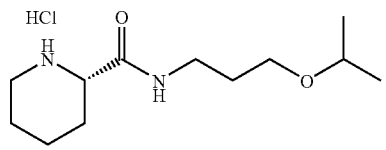

Compound I8 was prepared analogous to Example I6, starting from 3-isopropoxy-propylamine and BOC-protected L-pipecolinic acid. The crude salt was used as such.

MS (ESI): 229 [M+H]+

EXAMPLE I9

((S)-Piperidine-2-carboxylic acid (4-hydroxy-cyclohexyl)-amide hydrochloride (I9)

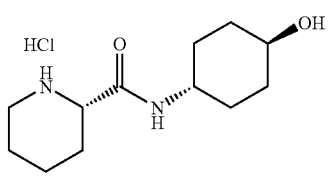

Compound I9 was prepared analogous to Example I6, starting from 4-hydroxy-cyclohexylamine and BOC-protected L-pipecolinic acid.

MS (ESI): 227 [M+H]+, ¹H-NMR (DMSO-d₆): δ (ppm) 9.3 (br d, 1H), 8.62 (m, 1H), 8.45 (d, 1H), 3.67 (m, 1H), 3.5 (m, 1H), 3.4 (m, 1H), 3.18 (m, 1H), 2.85 (m, 1H), 2.05 (m, 1H), 1.2-1.85 (m, 14H).

EXAMPLE I10

(S)-Piperidine-2-carboxylic acid isopropylamide hydrochloride (I10)

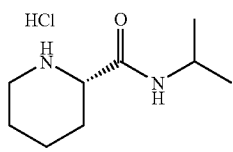

Compound I10 was prepared analogous to Example I6, starting from BOC-protected L-pipecolinic acid and propylamine.

¹H-NMR (DMSO-d₆): δ (ppm) 9.43 (broad s, 1H), 8.67 (broad s, 1H), 8.55 (broad s, 1H), 3.86 (m, 1H), 3.67 (m, 1H), 3.19 (m, 1H), 2.85 (m, 1H), 2.08 (m, 1H), 1.35-1.85 (m, 5), 1.1 (d, 3H), 1.07 (d, 3H).

EXAMPLE I11

(S)-Piperidine-2-carboxylic acid cyclopropylamide hydrochloride (I11)

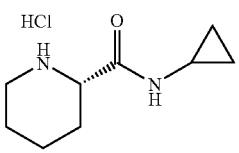

Compound I11 was prepared analogous to Example I6, starting from BOC-protected L-pipecolinic acid and cyclopropylamine.

¹H-NMR (DMSO-d₆): δ (ppm) 8.4-9.6 (broad s, 2H), 8.79 (d, 1H), 3.65 (m, 1H), 3.17 (m, 1H), 2.85 (m, 1H), 2.68 (m, 1H), 2.05 (m, 1H), 1.3-1.8 (m, 5H), 0.66 (m, 2H), 0.45 (m, 2H).

EXAMPLE I12

(S)-Piperidine-2-carboxylic acid benzylamide hydrochloride (I12)

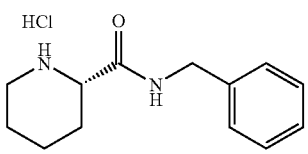

Compound I12 was prepared analogous to Example I6, starting from BOC-protected L-pipecolinic acid and benzylamine.

¹H-NMR (DMSO-d₆): δ (ppm) 9.47 (broad d, 1H), 9.22 (broad t, 1H), 8.73 (broad q, 1H), 7.2-7.4 (m, 5H), 4.34 (d, 2H), 3.82 (m, 1H), 3.2 (m, 1H), 2.89 (m, 1H), 2.16 (m, 1H), 1-1.85 (m, 5H).

EXAMPLE I13

(S)-Piperidine-2-carboxylic acid phenylamide hydrochloride (I13)

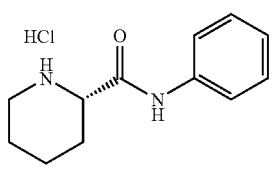

Compound I13 was prepared analogous to Example I6, starting from BOC-protected L-pipecolinic acid and aniline.

¹H-NMR (DMSO-d₆): δ (ppm) 10.97 (broad s, 1H), 9.5 (broad d, 1H), 8.83 (broad q, 1H), 7.68 (m, 2H), 7.35 (m, 2H), 7.1 (m, 1H), 3.98 (m, 1H), 3.25 (m, 1H), 2.94 (m, 1H), 2.28 (m, 1H). 1.45-1.9 (m, 5H).

EXAMPLE I14

(S)-Piperidine-2-carboxylic acid (4-fluoro-phenyl)-amide hydrochloride (I14)

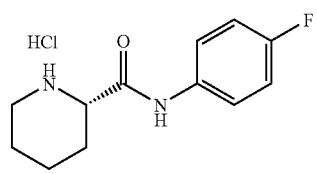

Compound I14 was prepared analogous to Example I6, starting from BOC-protected L-pipecolinic acid and (S)-1-phenyl-ethylamine. The crude salt was used as such.

EXAMPLE I15

(S)-3-Isobutylcarbamoyl-piperazine-1-carboxylic acid .tert.-butyl ester (I15)

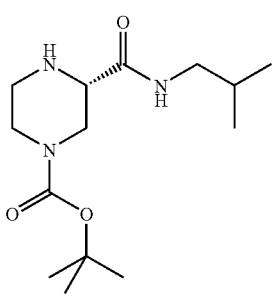

Compound I15 was prepared analogous to Step A of Example I4, starting from isobutylamine and (S)-Piperazine-1,2,4-tricarboxylic acid 1-benzyl ester 4-tert-butyl ester (prepared according the procedure described in *Tetrahedron Letters* 1989, 30, 5193) followed by heterogeneous catalytic hydrogenation using Pd/C (10%) in methanol.

$^1$H-NMR (DMSO-$d_6$): δ (ppm) 7.83 (broad s, 1H), 2.7-4.2 (very broad multiplets, 9H), 1.7 (m, 1H), 1.39 (s, 9H), 0.82 (d, 3H).

Synthesis of the Hydroxamic Acids I'''

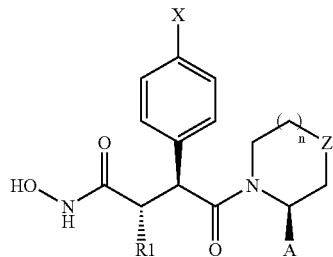

The hydroxamic acids of the formula I''' were prepared by the general Method A which comprises the coupling of intermediates VII' with the corresponding amines VIII' or their appropriately protected forms, followed by an ozonolysis of the vinyl olefin, coupling with O-(trimethylsilyl)-hydroxylamine and deprotection if required.

Method A is illustrated by the following representative example 1.

EXAMPLE 1

3(S)-(4-Chloro-phenyl)-2(S)-ethyl-N-hydroxy-4-morpholin-4-yl-4-oxo-butyramide (1)

Step A: 2(S)-(4-Chloro-phenyl)-3(S)-ethyl-1-morpholin-4-yl-pent-4-en-1-one (1a)

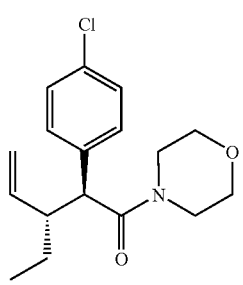

Morpholine (0.107 ml, 1.23 mmol) and the intermediate I2 (239 mg, 1.12 mmol) were dissolved in 5 ml of DMF and cooled in an ice-bath. HOBT (188 mg, 1.23 mmol), triethylamine (0.309 ml, 2.24 mmol) and EDC (214 mg, 1.12 mmol) were added successively. The ice-bath was removed and stirring continued over night. The mixture was evaporated, redissolved in diethyl ether and extracted with 2N-HCl (twice), 5% sodium bicarbonate and brine. The organic layer was dried over anhydrous sodium sulfate and evaporated to give a pale yellow oil. Yield (crude): 320 mg (93%).

MS (ESI): 308.1 [M+H]$^+$ $^1$H-NMR (CDCl$_3$): δ (ppm) 7.05-7.2 (m, 4H), 5.12-5.24 (m, 1H), 4.6-4.77 (m, 2H), 3.1-3.65 (m, 9H), 2.69 (q×d, 1H), 1.54 (m, 1H), 1.12 (m, 1H), 0.8 (t, 3H).

Step B: 3(S)-(4-Chloro-phenyl)-2(S)-ethyl-4-morpholin-4-yl-4-oxo-butyric acid (1b)

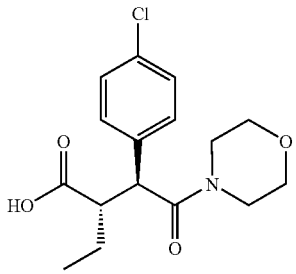

The crude olefin 1a (315 mg, 1.02 mmol) was dissolved in 15 ml of methanol and cooled to −75° C. A constant flow (50 l/h) of ozone was introduced at a temperature around −70° C. After about 10 minutes all starting material was consumed a blue colour appeared. The solution was then purged with nitrogen and dimethylsulfide (0.375 ml, 5.1 mmol) was added. The cooling bath was removed and stirring continued for 2 hours. The solvents were evaporated and the crude oil redissolved in 7 ml of t-butanol. A solution of sodium dihydrogenphosphate monohydrate (423 mg, 3.06 mmol) in 2 ml of water was added, followed by 2-methyl-2-butene (0.54 ml, 5.1 mmol) and sodium chlorite (185 mg, 2.04 mmol) in 2 ml of water. The mixture turns yellow and an exothermic reaction is observed (eventual cooling with ice-bath may be required for large scale reactions). After 1 hour the reaction had ceased and the colourless solution was treated with sodium sulfite (129 mg, 1.02 mmol) in 2 ml of water. Most of the solvents were then evaporated and the residue was partitioned between diethyl ether and 1N-HCl. The organic layer was separated and extracted twice with 1N-NaOH. The aqueous layers were combined, acidified with cold concentrated HCl and extracted three times with diethyl ether. The combined organic layers were then washed with water and brine and dried over anhydrous sodium sulfate. After evaporation a white foam was obtained. Yield (crude): 318 mg (95 %).

MS (ESI): 326.1 [M+H]$^+$ $^1$H-NMR (CDCl$_3$): δ (ppm) 7.1-7.3 (m, 4H), 4.82 (d, 1H), 3.2-3.7 (m, 8H), 3.07 (d×d×d, 1H), 1.6 (m, 2H), 0.88 (t, 3H).

Step C: 3(S)-(4-Chloro-phenyl)-2(S)-ethyl-N-hydroxy-4-morpholin-4-yl-4-oxo-butyramide (1)

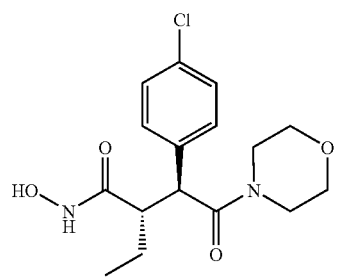

The crude acid 1b (310 mg, 0.95 mmol) was dissolved in 5 ml of dichloromethane. HOPO (111 mg, 1 mmol) and MEI (0.159 ml, 1.14 mmol) were added successively. The mixture was stirred for 30 minutes, then TMSONH2 (0.233 ml, 1.9 mmol) was added. After one hour another portion of TMSONH2 (0.233 ml, 1.9 mmol) was added and stirring continued over night. The reaction mixture was filtered (solid contained mostly HOPO) diluted with 20 ml of dichloromethane and extracted twice with 2N-HCl and brine, dried over anhydrous sodium sulfate and evaporated. The crude solid (237 mg, 73%) was purified by preparative HPLC (methanol/water=1/1). Yield: 100 mg (31%).

MS (ESI): 341.1 [M+H]$^+$ $^1$H-NMR (DMSO-d$_6$): δ (ppm) 10.28 (s, 1H), 8.55 (s, 1H), 7.32 (s, 4H), 4.12 (d, 1H), 3.15-3.75 (m, 8H), 2.77 (t×d, 1H), 1.45 (m, 2H), 0.82 (t, 3H).

EXAMPLE 2

2(R)-Benzyloxymethyl-4-[4-(4-chloro-phenyl)-piperazin-1-yl]-N-hydroxy-3(S)-(4-methoxy-phenyl)-4-oxo-butyramide (2)

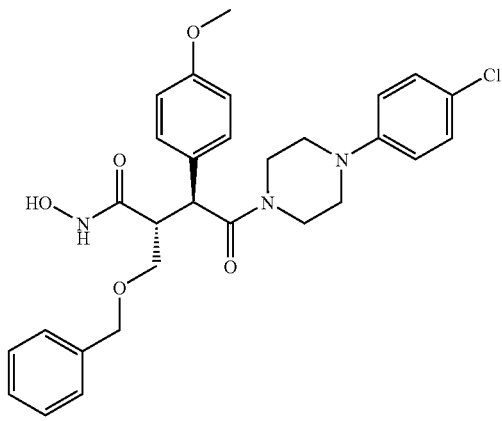

Compound 2 was prepared analogous to steps A to C of example 1, starting from 1-(4-chloro-phenyl)-piperazine and intermediate I1.

MS (neg. ESI): 536.2 [M–H]$^-$ $^1$H-NMR (DMSO-d$_6$): δ (ppm) 10.3 (s, 1H), 8.57 (s, 1H), 7.15-7.37 (m, 9H), 6.87 (d, 2H), 6.82 (d, 2H), 4.45 (AB system, 2H), 4.11 (d, 1H), 3.77 (m, 1H), 3.72 (s, 3H), 3.38-3.66 (m, 5H), 3.26 (m, 1H), 2.95 (m, 3H), 2.68 (m, 1H).

EXAMPLE 3

2(R)-Benzyloxymethyl-N-hydroxy-3(S)-(4-methoxy-phenyl)-4-oxo-4-piperidin-1-yl-butyramide (3)

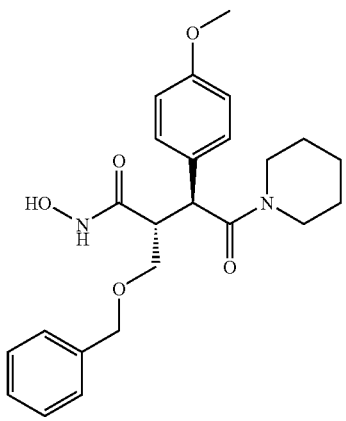

Compound 3 was prepared analogous to steps A to C of example 1, starting from piperidine and intermediate I1.

MS (ESI): 427.2 [M+H]$^+$, 449.2 [M+Na]$^+$ $^1$H-NM (DMSO-d$_6$): δ (ppm) 10.29 (s, 1H), 8.56 (s, 1H), 7.25-7.4 (m, 5H), 7.21 (d, 2H), 6.81 (d, 2H), 4.45 (AB system, 2H), 3.72 (s, 3H), 3.3-3.65 (m, 6H), 3.23 (m, 1H), 0.85-1.55 (m, 6H).

EXAMPLE 4

N-Hydroxy-2(R)-hydroxymethyl-3(S)-(4-methoxy-phenyl)-4-oxo-4-piperidin-1-yl-butyramide (4)

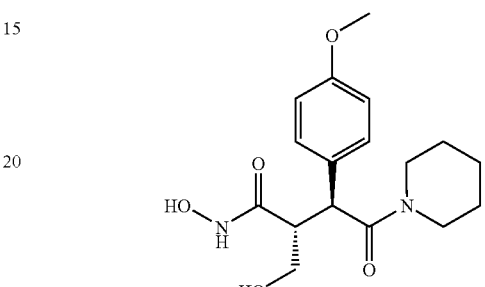

A solution of hydroxamic acid 3 (330 mg, 0.64 mmol) in 20 ml of methanol was hydrogenated under normal pressure with 70 mg of palladium on barium sulfate for about 5 hours. After filtration of the catalyst the solvent was evaporated and the crude product was purified by preparative HPLC to give a white solid. Yield: 133 mg (62%).

MS (ESI): 337.0 [M+H]$^+$, 359.0 [M+Na]$^+$ $^1$H-NMR (DMSO-d$_6$): δ (ppm) 10.2 (broad s, 1H), 8.48 (broad s, 1H), 7.2 (d, 2H), 6.8 (d, 2H), 4.65 (broad s, 1H), 4.0 (d, 1H), 3.3-3.6 (m, 6H), 2.97 (m, 1H), 0.9-1.7 (m, 6H).

EXAMPLE 5

(S)-4-[(2S,3S)-2-(4-Chloro-phenyl)-3-hydroxycarbamoyl-pentanoyl]-3-isobutylcarbamoyl-piperazine-1-carboxylic acid .tert-butyl ester (5)

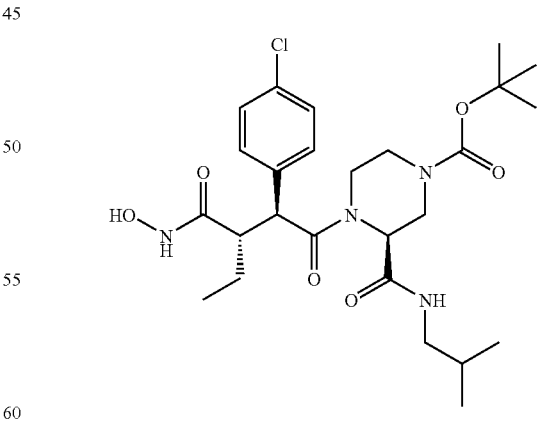

Compound 5 was prepared analogous to Steps A to C of Example 1, starting from amine I15 and succinate I2.

MS (neg. ESI): 537.0 [M–H]$^-$ MS (pos. ESI): 561.0 [M+Na]$^+$, 577.0 [M+K]$^+$, 461.0 [M–BOC]$^+$ $^1$H-NMR (DMSO-d$_6$): 2 rotamers at 20° C. (ratio 3:2) δ (ppm) 10.25 (broad s, 1H), 8.56 and 8.53 (broad s, 1H), 8.27 and 7.66

(broad s, 1H), 7.2-7.4 (m, 4H), 4.73 and 4.53 (broad d, 1H), 2.4-4.25 (overlapping broad multiplets, 10H), 1.2-1.85 (overlapping broad multiplets, 3H), 1.35 (s, 9H), 0.7-1.0 (overlapping multiplets, 9H).

EXAMPLE 6

(S)-1-[(2S,3S)-2-(4-Chloro-phenyl)-3-hydroxycarbamoyl-pentanoyl]-piperazine-2-carboxylic acid isobutyl-amide trifluoro-acetate (6)

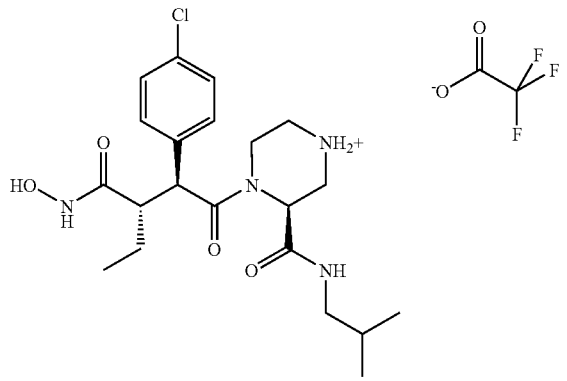

A solution of 5 (20 mg, 0.037 mmol) in 2.5 ml of dichloromethane was cooled in an ice-bath. It was then treated with TFA (29 µl, 0.37 mmol) and stirred at room temperature over night. After addition of 5 ml of toluene, the mixture was evaporated to give the crude TFA-salt.

Yield: 18 mg (88%). MS (neg. ESI): 437.0 [M−H]⁻, 551.0 [M+CF₃COO]⁻ MS (pos. ESI): 439.0 [M+H]⁺, 406.0 [M−NH−OH]⁺ ¹H-NMR (DMSO-d₆): 2 rotamers at 20° C. (ratio 3:1) δ (ppm) 10.3 and 10.28 (broad s, 1H), 9.24 and 9.0 and 8.57 and 8.23 (very broad singlets, together 3H), 8.41 and ~7.3 overlapping with aromatic signals (broad t, 1H), 7.15-7.45 (m, 4H), 5.11 and 4.92 (broad d, 1H), 4.4 and 4.37 (broad d, 1H), 4.23 and 4.01 (d, 1H), 2.6-3.3 (overlapping multiplets, 8H), 1.5 (m, 2H), 0.55-1.25 (overlapping multiplets, 9H).

EXAMPLE 7

1-[4-Benzyloxy-3(R)-hydroxycarbamoyl-2(S)-(4-methoxy-phenyl)-butyryl]-piperidine-2(S)-carboxylic acid methylamide (7)

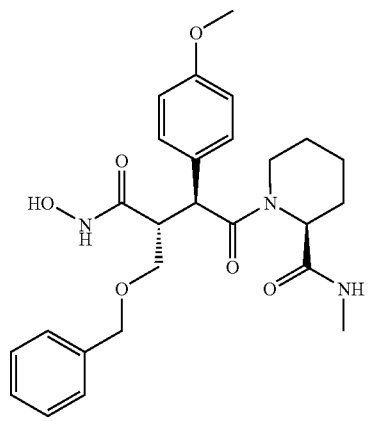

Compound 7 was prepared analogous to steps A to C of example 1, starting from piperidine-2(S)-carboxylic acid methylamide hydrochloride, I5, and intermediate I1.

MS (ESI): 484.2 [M+H]⁺, 506.2 [M+Na]⁺ ¹H-NMR (DMSO-d₆): 2 rotamers at 20° C. (ratio 2:3) δ (ppm) 10.3 and 10.26 (s, 1H), 8.56 and 8.53 (s, 1H), 7.83 and 7.13 (broad q, 1H), 7.25-7.6 (m, 5H), 7.21 (m, 2H), 6.83 (m, 2H), 4.93 and 4.6 (m, 1H), 4.36-4.56 (m, 2H), 4.32 and 3.96 (m, 1H), 4.1 and 3.79 (d, 1H), 3.73 (s, 3H), 2.96-3.68 (m, 4H), 2.62 and 2.47 (d, 3H), 1.94 (m, 1H), 0.65-1.65 (m, 5H).

EXAMPLE 8

1-[4-Hydroxy-3(R)-hydroxycarbamoyl-2(S)-(4-methoxy-phenyl)-butyryl]-piperidine-2(S)-carboxylic acid methylamide (8)

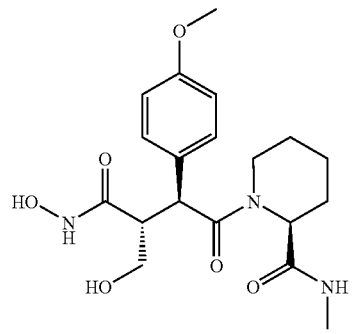

A solution of hydroxamic acid 7 (100 mg, 0.21 mmol) in 20 ml of methanol was hydrogenated under normal pressure with 50 mg of palladium on barium sulfate for about 5 hours. After filtration of the catalyst the solvent was evaporated and the crude product was purified by preparative HPLC to give a white solid. Yield: 53 mg (65%).

MS (ESI): 394.2 [M+H]⁺, 416.1 [M+Na]⁺ ¹H-NMR (DMSO-d₆): 2 rotamers at 20° C. (ratio 3:2) δ (ppm) 10.18 and 10.16 (s, 1H), 8.46 and 8.44 (s, 1H), 7.4 and 7.13 (broad q, 1H), 7.2 (m, 2H), 6.8 (m, 2H), 4.97 and 4.74 (m, 1H), 4.66 (broad s, 1H), 4.33 and 3.99 (m, 1H), 4.09 and 3.84 (d, 1H), 3.72 (s, 3H), 3.4-3.6 (m, 2H), 2.9-3.15 and 2.55-2.7 (m, 2H), 2.67 and 2.48 (d, 3H), 1.98 (m, 1H), 0.75-1.65 (m, 5M).

EXAMPLE 9

1-[3(S)-Hydroxycarbamoyl-2(S)-(4-methoxy-phenyl)-pentanoyl]-piperidine-2S-carboxylic acid methylamide (9)

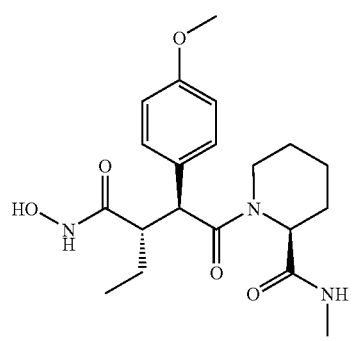

Compound 9 was prepared analogous to steps A to C of example 1, starting from piperidine-2(S)-carboxylic acid methylamide hydrochloride amine I5, and intermediate I3.

MS (neg. ESI): 390.1 [M–H]⁻, 425.8 [M–Cl]⁻ ¹H-NMR (DMSO-d₆): 2 rotamers at 20° C. (ratio 1:1) δ (ppm) 10.23 and 10.18 (s, 1H), 7.91 and 7.15 (broad q, 1H), 7.19 (m, 2H), 6.8 (m, 2H), 4.98 and 4.62 (m, 1H), 4.33 and 4.03 (m, 1H), 4.07 and 3.77 (d, 1H), 3.72 (s, 3H), 2.6-3.2 (m, 2H), 2.66 and 2.47 (d, 3H), 2.01 and 1.91 (d, 1H), 1.1-1.7 (m, 8H), 0.7-0.90 (m, 3H).

EXAMPLE 10

(S)-1-[(2S,3S)-3-Hydroxycarbamoyl-2-(4-methoxy-phenyl)-pentanoyl]-piperidine-2-carboxylic acid cyclopropylamide (10)

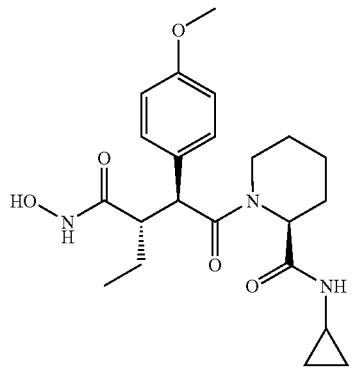

Compound 10 was prepared analogous to steps A to C of example 1, starting from amine I11 and succinate I3.

MS (neg. ESI): 416.1 [M–H]⁻ MS (pos. ESI): 440.1 [M+Na]⁺ ¹H-NMR (DMSO-d₆): 2 rotamers at 20° C. (ratio 1:1) δ (ppm) 10.23 and 10.2 (s, 1H), 8.53 and 8.47 (s, 1H), 8.07 and 7.08 (broad d, 1H), 7.2 (m, 2H), 6.7 (m, 2H), 4.93 and 4.6 (m, 1H), 3.9-4.4 (overlapping multiplets, 3H), 3.74 and 3.72 (s, 3H), 2.65-3.15 (overlapping multiplets, 2H), 1.98 and 1.88 (broad d, 1H), 0.1-1.7 (overlapping multiplets, 14H).

EXAMPLE 11

(S)-1-[(2S,3S)-3-Hydroxycarbamoyl-2-(4-methoxy-phenyl)-pentanoyl]-piperidine-2-carboxylic acid (2-methoxy-ethyl)-amide (11)

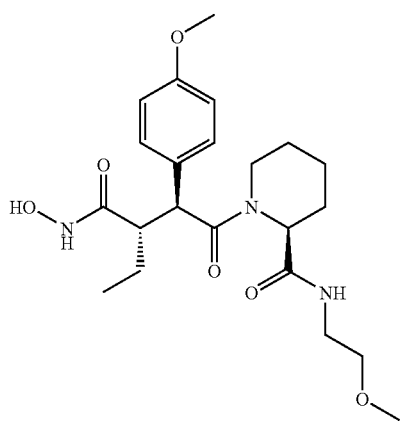

Compound 11 was prepared analogous to steps A to C of example 1, starting from amine I7 and succinate I3.

MS (neg. ESI): 390.1 [M–H]⁻, 425.8 [M–Cl]⁻ ¹H-NMR DMSO-d₆): 2 rotamers at 20° C. (ratio 1:1) δ (ppm) 10.23 and 10.18 (s, 1H), 7.91 and 7.15 (broad q, 1H), 7.19 (m, 2H), 6.8 (m, 2H), 4.98 and 4.62 (m, 1H), 4.33 and 4.03 (m, 1H), 4.07 and 3.77 (d, 1H), 3.72 (s, 3H), 2.6-3.2 (m, 2H), 2.66 and 2.47 (d, 3H), 2.01 and 1.91 (d, 1H), 1.1-1.7 (m, 8H), 0.7-0.90 (m, 3H).

EXAMPLE 12

(S)-1-[(2S,3S)-3-Hydroxycarbamoyl-2-(4-methoxy-phenyl)-pentanoyl]-piperidine-2-carboxylic acid (4-hydroxy-cyclohexyl)-amide (12)

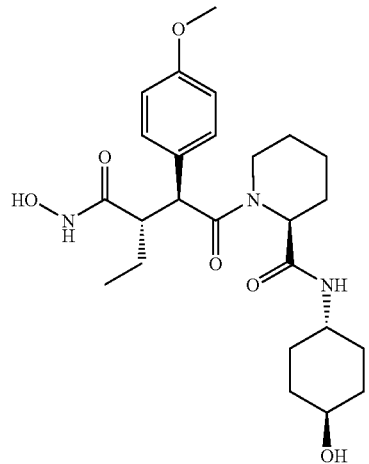

Compound 12 was prepared analogous to steps A to C of example 1, starting from amine I9 and succinate I3.

MS (neg. ESI): 390.1 [M–H]⁻, 425.8 [M–Cl]⁻ ¹H-NMR (DMSO-d₆): 2 rotamers at 20° C. (ratio 1:1) δ (ppm) 10.23 and 10.18 (s, 1H), 7.91 and 7.15 (broad q, 1H), 7.19 (m, 2H), 6.8 (m, 2H), 4.98 and 4.62 (m, 1H), 4.33 and 4.03 (m, 1H), 4.07 and 3.77 (d, 1H), 3.72 (s, 3H), 2.6-3.2 (m, 2H), 2.66 and 2.47 (d, 3H), 2.01 and 1.91 (d, 1H), 1.1-1.7 (m, 8H), 0.7-0.90 (m, 3H).

EXAMPLE 13

(S)-1-[(2S,3S)-3-Hydroxycarbamoyl-2-(4-methoxy-phenyl)-pentanoyl]-piperidine-2-carboxylic acid benzylamide (13)

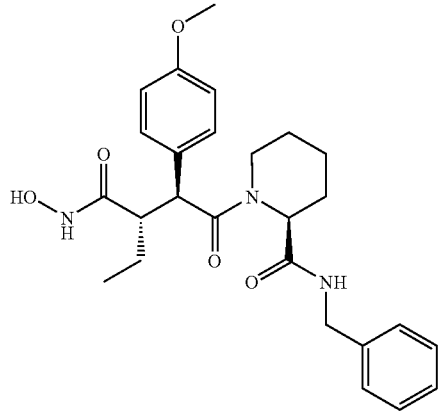

Compound 13 was prepared analogous to steps A to C of example 1, starting from amine I12 and succinate I3.

MS (neg. ESI): 466.1 [M–H]⁻ MS (pos. ESI): 490.0 [M+Na]⁺ ¹H-NMR (DMSO-d₆): 2 rotamers at 20° C. (ratio 1:1) δ (ppm) 10.22 and 10.19 (s, 1H), 8.52 and 8.48 (s, 1H), 8.59 and 7.7 (broad t, 1H), 6.7-7.4 (overlapping multiplets, 9H), 5.06 and 4.76 (m, 1H), 3.7-4.4 (overlapping multiplets, 4H), 3.73 and 3.70 (s, 3H), 3.05 and 2.92 (m, 1H), 2.72 (m, 1H), 2.08 and 1.97 (broad d, 1H), 1.2-1.7 (m, 6H), 0.95 (broad m, 1H), 0.82 and 0.76 (t, 3H).

EXAMPLE 14

(S)-1-[(2S,3S)-3-Hydroxycarbamoyl-2-(4-methoxy-phenyl)-pentanoyl]-piperidine-2-carboxylic acid (4-fluoro-phenyl)-amide (14)

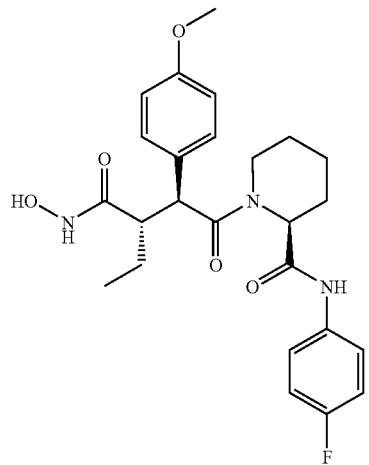

Compound 14 was prepared analogous to steps A to C of example 1, starting from amine I14 and succinate I3.

MS (neg. ESI): 470.0 [M–H]⁻ MS (pos. ESI): 494.1 [M+Na]⁺ ¹H-NMR (DMSO-d₆): 2 rotamers at 20° C. (ratio 2:1) δ (ppm) 10.21 (broad s, 1H), 10.06 and 9.73 (s, 1H), 8.51 and 8.47 (broad s, 1H), 6.7-7.7 (overlapping multiplets, 8H), 5.08 and 4.88 (m, 1H), 4.35 and 4.07 (broad d, 1H), 4.127 and 3.84 (d, 1H), 3.74 and 3.71 (s, 3H), 2.0-3.6 (overlapping multiplets, 3H), 0.95-1.75 (overlapping multiplets, 7H), 0.7-0.95 (overlapping multiplets, 3H).

EXAMPLE 15

(S)-1-[(2S,3S)-2-(4-Chloro-phenyl-3-hydroxycar-bamoyl-pentanoyl]-piperidine-2-carboxylic acid iso-propylamide (15)

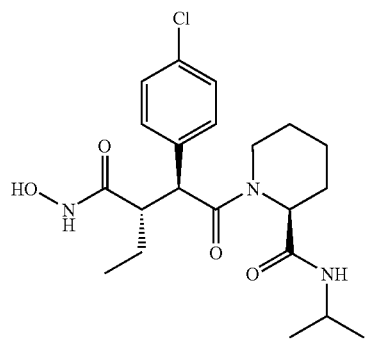

Compound 15 was prepared analogous to steps A to C of example 1, starting from amine I10 and succinate I2.

MS (neg. ESI): 422.0 [M–H]⁻ MS (pos. ESI): 446.0 [M+Na]⁺ ¹H-NMR (DMSO-d₆): 2 rotamers at 20° C. (ratio 3:2) δ (ppm) 10.28 and 10.25 (s, 1H), 8.55 and 8.50 (s, 1H), 7.84 and 6.77 (d, 1H), 7.25-7.5 (m, 4H), 4.95 and 4.65 (broad d, 1H), 4.3 and 4.08 (broad d, 1H), 4.17 and 3.89 (d, 1H), 3.92 and 3.72 (m, 1H), 3.0 (m, 1H), 2.75 (m, 1H), 2.05 and 1.93 (broad d, 1H), 1.2-1.7 (overlapping multiplets, 7H), 0.7-1.2 (overlapping multiplets, 9H).

EXAMPLE 16

(S)-1-[(2S,3S)-2-(4-Chloro-phenyl)-3-hydroxycar-bamoyl-pentanoyl]-piperidine-2-carboxylic acid cyclopropylamide (16)

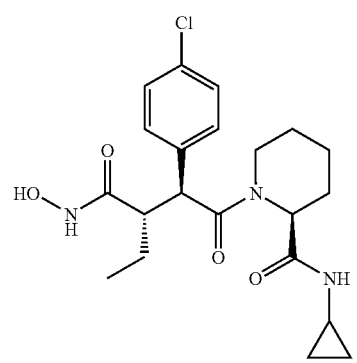

Compound 16 was prepared analogous to steps A to C of example 1, starting from amine I11 and succinate I2.

MS (neg. ESI): 420.1 [M–H]⁻ MS (pos. ESI): 44.0 [M+Na]⁺ ¹H-NMR (DMSO-d₆): 2 rotamers at 20° C. (ratio 1:1) δ (ppm) 10.25 (broad s, 1H), 8.55 and 8.51 (broad s, 1H), 8.09 and 7.48 (broad d, 1H), 7.3 (m, 4H), 4.91 and 4.6 (broad s, 1H), 4.28 and 4.03 (broad d, 1H), 4.15 and 3.84 (d, 1H), 3.08 and 2.94 (m, 1H), 2.7 (m, 1H), 1.97 and 1.89 (broad d, 1H), 0.15-1.75 (overlapping multiplets, 15H).

EXAMPLE 17

(S)-1-[(2S,3S)-2-(4-Chloro-phenyl)-3-hydroxycar-bamoyl-pentanoyl]-piperidine-2-carboxylic acid (3-isopropoxy-propyl)-amide (17)

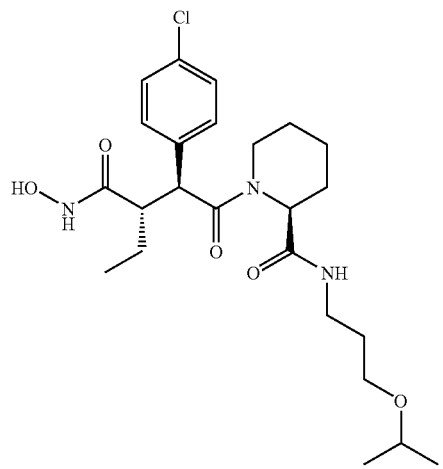

Compound 17 was prepared analogous to steps A to C of example 1, starting from amine I8 and succinate I2.1

MS (neg. ESI): 390.1 [M–M]⁻, 425.8 [M–Cl]⁻ ¹H-NMR (DMSO-d₆): 2 rotamers at 20° C. (ratio 1:1) δ (ppm) 10.23 and 10.18 (s, 1H), 7.91 and 7.15 (broad q, 1H), 7.19 (m, 2H), 6.8 (m, 2H), 4.98 and 4.62 (m, 1H), 4.33 and 4.03 (m, 1H), 4.07 and 3.77 (d, 1H), 3.72 (s, 3H), 2.6-3.2 (m, 2H), 2.66 and 2.47 (d, 3H), 2.01 and 1.91 (d, 1H), 1.1-1.7 (m, 8H), 0.7-0.90 (m, 3H).

EXAMPLE 18

(S)-1-[(2S,3S)-2-(4-Chloro-phenyl)-3-hydroxycarbamoyl-pentanoyl]-piperidine-2-carboxylic acid (4-hydroxy-cyclohexyl)-amide (18)

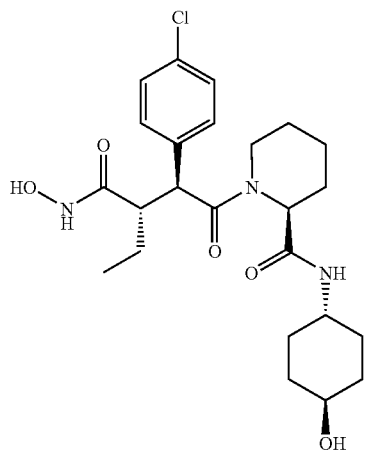

Compound 18 was prepared analogous to steps A to C of example 1, starting from amine I9 and succinate I2.

MS (neg. ESI): 390.1 [M–H]⁻, 425.8 [M–Cl]⁻ ¹H-NMR (DMSO-d₆): 2 rotamers at 20° C. (ratio 1:1) δ (ppm) 10.23 and 10.18 (s, 1H), 7.91 and 7.15 (broad q, 1H), 7.19 (m, 2H), 6.8 (m, 2H), 4.98 and 4.62 (m, 1H), 4.33 and 4.03 (m, 1H), 4.07 and 3.77 (d, 1H), 3.72 (s, 3H), 2.6-3.2 (m, 2H), 2.66 and 2.47 (d, 3H), 2.01 and 1.91 (d, 1H), 1.1-1.7 (m, 8H), 0.7-0.90 (m, 3H).

EXAMPLE 19

(S)-1-[(2S,3S)-2-(4-Chloro-phenyl)-3-hydroxycarbamoyl-pentanoyl]-2-carboxylic acid benzylamide (19)

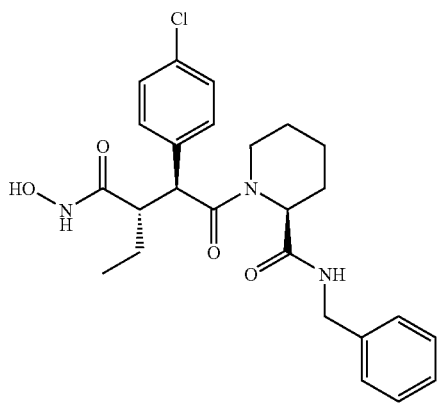

Compound 19 was prepared analogous to steps A to C of example 1, starting from amine I12 And succinate I2

MS (neg. ESI): 470.0 [M–H]⁻ MS (pos. ESI): 494.0 [M+Na]⁺ ¹H-NMR (DMSO-d₆): 2 rotamers at 20° C. (ratio 55:45) δ (ppm) 10.25 (broad s, 1H), 8.55 and 8.52 (broad s, 1H), 8.6 and 7.95 (broad t, 1H), 7.05-7.65 (m, 9H), 5.04 and 4.78 (broad d, 1H), 3.88-4.42 (overlapping multiplets, 4H), 3.08 and 2.95 (m, 1H), 2.74 (m, 1H) 2.07 and 1.98 (broad d, 1H), 1.21.7 (m, 6H), 0.97 (m, 1H), 0.72 (t, 3H).

EXAMPLE 20

(S)-1-[(2S,3S)-2-(4-Chloro-phenyl)-3-hydroxycarbamoyl-pentanoyl]-piperidine-2-carboxylic acid phenylamide (20)

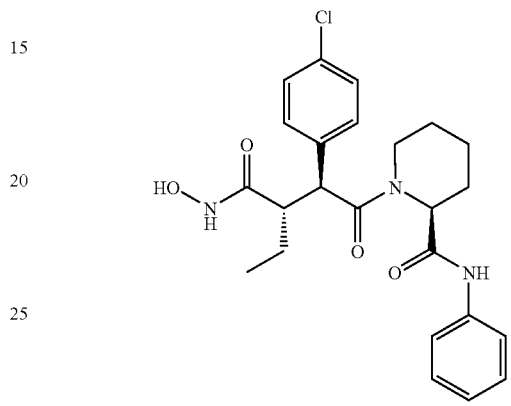

Compound 20 was prepared analogous to steps A to C of example 1, starting from amine I13 And succinate I2.

MS (neg. ESI): 446.0 [M-H]⁻ MS (pos. ESI): 480. [M+Na]⁺ ¹H-NMR (DMSO-d₆): 2 rotamers at 20° C. (ratio 2:1) δ (ppm) 10.25 (broad s, 1H), 10.05 and 9.7 (broad s, 1H), 8.5 (broad s, 1H), 6.95-7.7 (m, 9H), 5.08 and 4.9 (broad d, 1H), 4.34 and 4.07 (broad d, 1H), 4.17 and 3.93 (d, 1H), 3.23 and 3.09 (m, 1H), 2.72 (m, 1H), 0.90-2.15 (overlapping multiplets, 8H), 0.82 and 0.74 (t, 3H).

EXAMPLE 21

1-[3(S)-Hydroxycarbamoyl-2(S)-(4-methoxy-phenyl)-pentanoyl]-pyrrolidine-2(S)-carboxylic acid phenylamide (21)

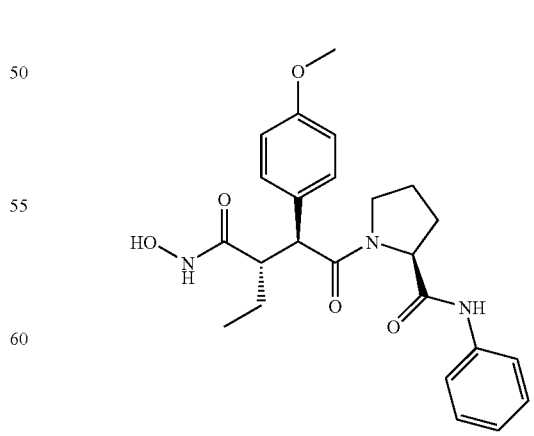

Compound 21 was prepared analogous to steps A to C of example 1, starting from amine I4 and succinate I3.

MS (neg. ESI): 438.0 [M–H]⁻, 474.0 [M–Cl]⁻ ¹H-NMR DMSO-d₆): 2 rotamers at 20° C. (ratio 2:1) δ (ppm) 10.3 and 10.22 (s, 1H), 10.15 and 9.86 (s, 1H), 8.5 and 8.42 (s, 1H), 6.7-7.7 (m, 9H), 4.47 (m, 1H), 3.85 and 3.5 (d, 1H), 3.68-3.78 and 3.57 (m, 1H), 3.72 (s, 3H), 3.46 and 3.28 (m, 1H), 2.56-2.75 (m, 1H), 1.2-2.65 (m, 6H), 0.81 and 0.74 (t, 3H).

10.2 and 9.9 (s, 1H), 8.55 and 8.45 (s, 1H), 6.95-7.7 (m, 9H), 4.46 (m, 1H), 3.93 and 3.56 (d, 1H), 3.74 and 3.59 (m, 1H), 3.44 and 3.28 (m, 1H), 2.58-2.77 (m, 1I), 1.2-2.45 (m, 6H), 0.82 and 0.75 (t, 3H).

The table below represents the above examples with the general formula Ia

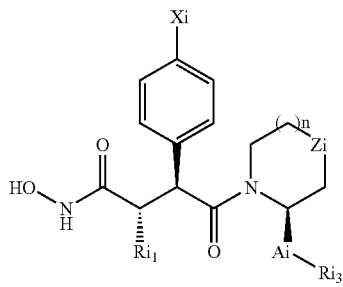

| Exp. | n | Zi | Ai | Ri₁ | Xi | Ri₃ |
|---|---|---|---|---|---|---|
| 1 | 1 | O | H | Ethyl | Cl | |
| 2 | 1 | N-4-Chlorophenyl | H | CH₂—O-Benzyl | OMe | |
| 3 | 1 | CH₂ | H | CH₂—O-Benzyl | OMe | |
| 4 | 1 | CH₂ | H | CH₂—OH | OMe | |
| 5 | 1 | N—BOC | —CO—NH— | Ethyl | Cl | iso-Butyl |
| 6 | 1 | NH | —CO—NH— | Ethyl | Cl | iso-Butyl |
| 7 | 1 | CH₂ | —CO—NH— | CH₂—O-Benzyl | OMe | Methyl |
| 8 | 1 | CH₂ | —CO—NH— | CH₂—OH | OMe | Methyl |
| 9 | 1 | CH₂ | —CO—NH— | Ethyl | OMe | Methyl |
| 10 | 1 | CH₂ | —CO—NH— | Ethyl | OMe | Cyclo-Propyl |
| 11 | 1 | CH₂ | —CO—NH— | Ethyl | OMe | 2-Methoxy-ethyl |
| 12 | 1 | CH₂ | —CO—NH— | Ethyl | OMe | 4-Hydroxy-cyclohexyl |
| 13 | 1 | CH₂ | —CO—NH— | Ethyl | OMe | Benzyl |
| 14 | 1 | CH₂ | —CO—NH— | Ethyl | OMe | 4-Fluoro-phenyl |
| 15 | 1 | CH₂ | —CO—NH— | Ethyl | Cl | iso-Propyl |
| 16 | 1 | CH₂ | —CO—NH— | Ethyl | Cl | cyclo-Propyl |
| 17 | 1 | CH₂ | —CO—NH— | Ethyl | Cl | 3-Isopropoxy-propyl |
| 18 | 1 | CH₂ | —CO—NH— | Ethyl | Cl | 4-Hydroxy-cyclohexyl |
| 19 | 1 | CH₂ | —CO—NH— | Ethyl | Cl | Benzyl |
| 20 | 1 | CH₂ | —CO—NH— | Ethyl | Cl | Phenyl |
| 21 | 0 | CH₂ | —CO—NH— | Ethyl | OMe | Phenyl |
| 22 | 0 | CH₂ | —CO—NH— | Ethyl | Cl | (S)-2-Hydroxy-propyl |

EXAMPLE 22

(S)-1-[(2S,3S)-2-(4-Chloro-phenyl)-3-hydroxycarbamoyl-pentanoyl]-pyrrolidine-2-carboxylic acid ((S)-2-hydroxy-propyl)-amide (22)

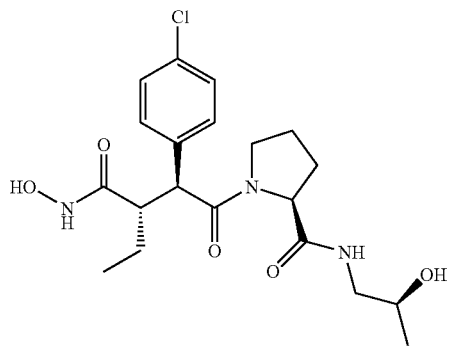

Compound 22 was prepared analogous to steps A to C of example 1, starting from amine I6 and intermediate I2.

MS (neg. ESI): 442.2 [M–H]⁻ ¹H-NMR (DMSO-d₆): 2 rotamers at 20° C. (ratio 2:1) δ (ppm) 10.34 and 10.26 (s, 1H),

The invention claimed is:

1. A compound of Formula I

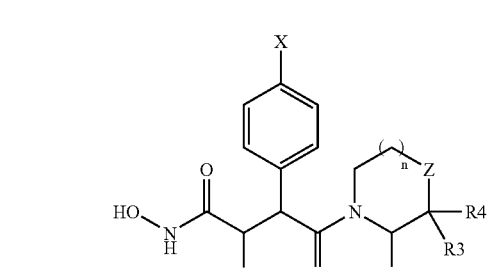

wherein

R₁ is lower alkyl, $C_3$-$C_8$cycloalkyl, $C_3$-$C_{18}$heterocycloalkyl or $C_4$-$C_{18}$aryl each of which is independently optionally substituted by hydroxy, halogen, lower alkoxy, $C_3$-$C_8$cycloalkyl-lower alkoxy, or $C_4$-$C_{18}$ aryl-lower alkoxy;

X is halogen, cyano, lower alkyl, halo-substituted lower alkyl, $C_4$-$C_{18}$aryl, $C_4$-$C_{18}$aryl-lower alkyl, hydroxy, —OR₅, SR₅ or —NR₆R₇, each of which is optionally substituted by halogen, hydroxy, lower alkoxy, C₃-C₆cycloalkyl-lower alkoxy, or C₄-C₁₈aryl-lower alkoxy
wherein
R₅ is hydrogen, lower alkyl, C₃-C₈cycloalkyl, C₃-C₁₈heterocycloalkyl or C₄-C₁₈aryl and
R₆ and R₇ are independently H, lower alkyl, C₃-C₈cycloalkyl, C₃-C₁₈heterocycloalkyl or C₄-C₁₈aryl;

Z is —CH₂—, —CHR₈—, —O—, —S—, or —N(R₈)—
wherein
R₈ is H, lower alkyl, C₃-C₈cycloalkyl, C₃-C₁₈heterocycloalkyl, C₄-C₁₈aryl lower alkoxycarbonyl or C₄-C₈aryloxycarbonyl, each of which is independently optionally substituted by halogen, hydroxy, lower alkoxy, C₃-C₆cycloalkyl-lower alkoxy, or C₄-C₈aryl-lower alkoxy;

A is hydrogen, —CR₁₀R₁₁-Q-R₁₂, —C(O)-Q-R₁₂ or —C(S)-Q-R₁₂
wherein
R₁₀ and R₁₁ are independently H, lower alkyl, C₃-C₈cycloalkyl, C₃-C₁₈heterocycloalkyl or C₄-C₁₈aryl each of which is independently optionally substituted by halogen, hydroxy, lower alkoxy, C₃-C₆cycloalkyl-lower alkoxy, or C₄-C₁₈ aryl-lower alkoxy,
Q is —NR₈—, —S— or —O—, where R₈ is as defined above, and
R₁₂ is lower alkyl C₃-C₈cycloalkyl, C₄-C₁₈aryl, C₄-C₁₈aryl-lower alkyl, each optionally substituted by hydroxy, halogen, lower alkoxy, C₃-C₆cycloalkyl, C₃-C₆cycloalkoxy, C₄-C₁₈aryl or C₄-C₁₈aryl-lower alkoxy; and
R₃ and R₄ is Hydrogen or lower alkyl; and
n is 0 or 1, or a pharmaceutically-acceptable and -cleavable ester thereof or acid addition salts thereof.

2. A compound according to claim 1 of formula II

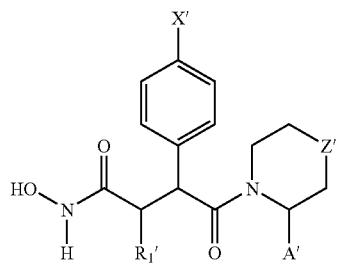

II wherein
R₁' is H, lower alkyl or C₃-C₈cycloalkyl, each of which is optionally substituted by hydroxy, halogen, lower alkoxy or C₄-C₁₈aryl-lower alkoxy;
X' is halogen, cyano, lower alkyl, halo-substituted lower alkyl or lower alkoxy, each of which is optionally substituted by halogen, hydroxy or lower alkoxy;
Z' is —CH₂— or —N(R'₈)— wherein R'₈ is H, lower alkyl, C₄-C₁₈aryl (optionally substituted by halogen), lower alkoxycarbonyl or C₄-C₁₈aryloxycarbonyl;
A' is H or —C(O)-Q'-R₁₂' wherein Q' is —S— or —O— and R₁₂' is lower alkyl, C₃-C₈ cycloalkyl, C₄-C₁₈aryl, each optionally substituted by hydroxy, halogen, lower alkoxy, C₃-C₈cycloalkyl, or C₄-C₁₈aryl, or a pharmaceutically acceptable and cleavable ester thereof or acid addition salts thereof.

3. A compound according to claim 1 of formula I' or formula II'

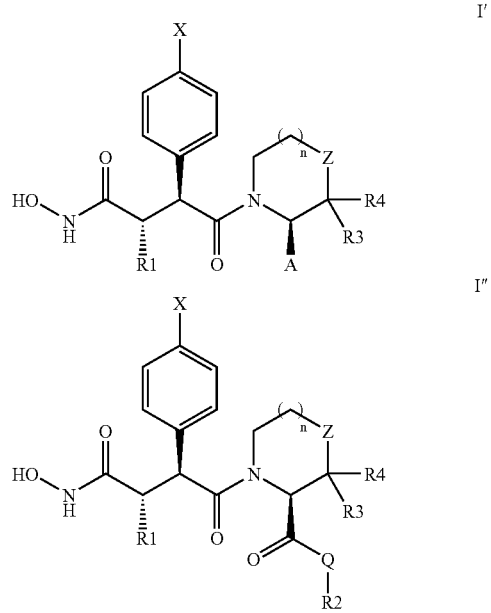

wherein the symbols are as defined above.

4. A compound according to claim 1 selected from:
3(S)-(4-Chloro-phenyl)-2(S)-ethyl-N-hydroxy-4-morpholin-4-yl-4-oxo-butyramide;
2(R)-Benzyloxymethyl-4-[4-(4-chloro-phenyl)-piperazin-1-yl]-N-hydroxy-3(S)-(4-methoxy-phenyl)-4-oxo-butyramide;
2(R)-Benzyloxymethyl-N-hydroxy-3(S)-(4-methoxy-phenyl)-4-oxo-4-piperidin-1-yl-butyramide,
N-Hydroxy-2(R)-hydroxymethyl-3(S)-(4-methoxy-phenyl)-4-oxo-4-piperidin-1-yl-butyramide;
(S)-4-[(2S,3S)-2-(4-Chloro-phenyl)-3-hydroxycarbamoyl-pentanoyl]-3-isobutylcarbamoyl-piperazine-1-carboxylic acid tert-butyl ester;
(S)-1-[(2S,3S)-2-(4-Chloro-phenyl)-3-hydroxycarbamoyl-pentanoyl]-piperazine-2-carboxylic acid isobutylamide trifluoro-acetate;
1-[4-Benzyloxy-3(R)-hydroxycarbamoyl-2(S)-(4-methoxy-phenyl)-butyryl]-piperidine-2(S)-carboxylic acid methylamide;
1-[4-Hydroxy-3(R)-hydroxycarbamoyl-2(S)-(4-methoxy-phenyl)-butyryl]-piperidine-2(S)-carboxylic acid methylamide;
1-[3(S)-Hydroxycarbamoyl-2(S)-(4-methoxy-phenyl)-pentanoyl]-piperidine-2(S)-carboxylic acid methylamide;
(S)-1-[(2S,3S)-3-Hydroxycarbamoyl-2-(4-methoxy-phenyl)-pentanoyl]-piperidine-2-carboxylic acid cyclopropylamide;
(S)-1-[(2S,3S)-3-Hydroxycarbamoyl-2-(4-methoxy-phenyl)-pentanoyl]-piperidine-2-carboxylic acid (2-methoxy-ethyl)-amide;
(S)-1-[(2S,3S)-3-Hydroxycarbamoyl-2-(4-methoxy-phenyl)-pentanoyl]-piperidine-2-carboxylic acid (4-hydroxy-cyclohexyl)-amide;

(S)-1-[(2S,3S)-3-Hydroxycarbamoyl-2-(4-methoxy-phenyl)-pentanoyl]-piperidine-2-carboxylic acid benzylamide;

(S)-1-[(2S,3S)-3-Hydroxycarbamoyl-2-(4-methoxy-phenyl)-pentanoyl]-piperidine-2-carboxylic acid (4-fluoro-phenyl)-amide;

(S)-1-[(2S,3S)-2-(4-Chloro-phenyl)-3-hydroxycarbamoyl-pentanoyl]-piperidine-2-carboxylic acid isopropylamide;

(S)-1-[(2S,3S)-2-(4-Chloro-phenyl)-3-hydroxycarbamoyl-pentanoyl]-piperidine-2-carboxylic acid cyclopropylamide;

(S)-1-[(2S,3S)-2-(4-Chloro-phenyl)-3-hydroxycarbamoyl-pentanoyl]-piperidine-2-carboxylic acid (3-isopropoxy-propyl)-amide;

(S)-1-[(2S,3S)-2-(4-Chloro-phenyl)-3-hydroxycarbamoyl-pentanoyl]-piperidine-2-carboxylic acid (4-hydroxy-cyclohexyl)-amide;

(S)-1-[(2S,3S)-2-(4-Chloro-phenyl)-3-hydroxycarbamoyl-pentanoyl]-piperidine-2-carboxylic acid benzylamide;

(S)-1-[(2S,3S)-2-(4-Chloro-phenyl)-3-hydroxycarbamoyl-pentanoyl]-piperidine-2-carboxylic acid phenylamide;

1-[3(S)-Hydroxycarbamoyl-2(S)-(4-methoxy-phenyl)-pentanoyl]-pyrrolidine-2(S)-carboxylic acid phenylamide;

and (S)-1-[(2S,3S)-2-(4-Chloro-phenyl)-3-hydroxycarbamoyl-pentanoyl]-pyrrolidine-2-carboxylic acid ((S)-2-hydroxy-propyl)-amide;

or a pharmaceutically acceptable and cleavable ester thereof of acid addition salts thereof.

5. A method of inhibiting production of soluble TNF in a subject in need of such treatment which method comprises administering to said subject an effective amount of a compound according to claim 1.

6. A pharmaceutical composition comprising a compound according to claim 1 in association with a pharmaceutically acceptable diluent or carrier.

7. A method of inhibiting neuropathic pain in a subject in need of such treatment which method comprises administering to said subject an effective amount of a compound according to claim 1.

8. A process for the preparation of a compound of formula I

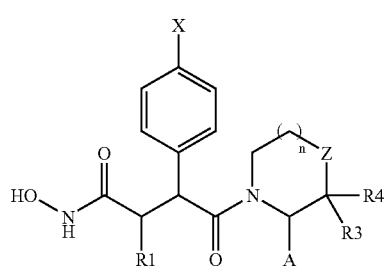

I wherein
$R_1$ is lower alkyl, $C_3$-$C_8$cycloalkyl, $C_3$-$C_{18}$heterocycloalkyl or $C_4$-$C_{18}$aryl each of which is independently optionally substituted by hydroxy, halogen, lower alkoxy, $C_3$-$C_8$cycloalkyl-lower alkoxy, or $C_4$-$C_{18}$ aryl-lower alkoxy;

X is halogen, cyano, lower alkyl, halo-substituted lower alkyl, $C_4$-$C_{18}$aryl, $C_4$-$C_{18}$aryl-lower alkyl, hydroxy, —$OR_5$, $SR_5$ or —$NR_6R_7$, each of which is optionally substituted by halogen, hydroxy, lower alkoxy, $C_3$-$C_6$cycloalkyl-lower alkoxy, or $C_4$-$C_{18}$aryl-lower alkoxy wherein
$R_5$ is hydrogen, lower alkyl, $C_3$-$C_8$cycloalkyl, $C_3$-$C_{18}$heterocycloalkyl or $C_4$-$C_{18}$aryl and $R_6$ and $R_7$ are independently H, lower alkyl, $C_3$-$C_8$cycloalkyl, $C_3$-$C_{18}$heterocycloalkyl or $C_4$-$C_{18}$aryl;

$C_{18}$heterocycloalkyl or $C_4$-$C_{18}$aryl;

Z is —$CH_2$—, —$CHR_8$—, —O—, —S—, or —$N(R_8)$—
wherein
$R_8$ is H, lower alkyl, $C_3$-$C_8$cycloalkyl, $C_3$-$C_{18}$heterocycloalkyl, $C_4$-$C_{18}$aryl lower alkoxycarbonyl or $C_4$-$C_8$aryloxycarbonyl, each of which is independently optionally substituted by halogen, hydroxy, lower alkoxy, $C_3$-$C_6$cycloalkyl-lower alkoxy, or $C_4$-$C_8$aryl-lower alkoxy;

A is hydrogen, —$CR_{10}R_{11}$-Q-$R_{12}$, —C(O)-Q-$R_{12}$ or —C(S)-Q-$R_{12}$
wherein
$R_{10}$ and $R_{11}$ are independently H, lower alkyl, $C_3$-$C_8$cycloalkyl, $C_3$-$C_{18}$heterocycloalkyl or $C_4$-$C_{18}$aryl each of which is independently optionally substituted by halogen, hydroxy, lower alkoxy, $C_3$-$C_6$cycloalkyl-lower alkoxy, or $C_4$-$C_{18}$ aryl-lower alkoxy, Q is —$NR_8$—, —S— or —O—, where $R_8$ is as defined above, and $R_{12}$ is lower alkyl $C_3$-$C_8$cycloalkyl, $C_4$-$C_{18}$aryl, $C_4$-$C_{18}$aryl-lower alkyl, each optionally substituted by hydroxy, halogen, lower alkoxy, $C_3$-$C_6$cycloalkyl, $C_3$-$C_6$cycloalkoxy, $C_4$-$C_{18}$aryl or $C_4$-$C_{18}$aryl-lower alkoxy; and $R_3$ and $R_4$ is Hydrogen or lower alkyl; and n is 0 or 1, or a pharmaceutically-acceptable and -cleavable ester thereof or acid addition salts thereof which process comprises converting a corresponding free carboxylic acid derivative of formula V

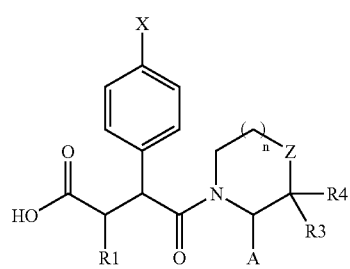

V wherein the symbols are as for Formula I, to the corresponding hydroxamic acid derivative of formula I.

9. A method of inhibiting matrix metalloproteinase activity in a subject in need of such treatment which method comprises administering to said subject an effective amount of a compound according to claim 1.

10. A method of reducing inflammation in a subject in need of such treatment which method comprises administering to said subject an effective amount of a compound according to claim 1.

11. A method of inducing immunosuppression in a subject in need of such treatment which method comprises administering to said subject an effective amount of a compound according to claim 1.

12. A method of treating neuropathic pain in a subject in need of such treatment which method comprises administering to said subject an effective amount of a compound according to claim 1.

* * * * *

UNITED STATES PATENT AND TRADEMARK OFFICE
CERTIFICATE OF CORRECTION

PATENT NO.       : 7,589,091 B2                                    Page 1 of 1
APPLICATION NO. : 10/511065
DATED            : September 15, 2009
INVENTOR(S)      : Janser et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 838 days.

Signed and Sealed this

Twenty-first Day of September, 2010

David J. Kappos
*Director of the United States Patent and Trademark Office*